(12) United States Patent
Ito et al.

(10) Patent No.: US 7,820,438 B2
(45) Date of Patent: Oct. 26, 2010

(54) PRIMARY CULTURED ADIPOCYTES FOR GENE THERAPY

(75) Inventors: Masashi Ito, Tsukuba (JP); Yasushi Saito, Chiba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/518,472

(22) PCT Filed: Jun. 18, 2003

(86) PCT No.: PCT/JP03/07721

§ 371 (c)(1),
(2), (4) Date: Oct. 4, 2005

(87) PCT Pub. No.: WO03/106663

PCT Pub. Date: Dec. 24, 2003

(65) Prior Publication Data

US 2006/0121008 A1    Jun. 8, 2006

(30) Foreign Application Priority Data

Jun. 18, 2002  (JP)  ............................ 2002-177648
Aug. 19, 2002  (JP)  ............................ 2002-237974

(51) Int. Cl.
 *C12N 5/00* (2006.01)
 *C12N 5/10* (2006.01)
 *A61K 48/00* (2006.01)
(52) U.S. Cl. ...................... 435/377; 424/93.2; 435/325; 435/360
(58) Field of Classification Search ................. 435/377, 435/325, 360; 424/93.2
 See application file for complete search history.

(56) References Cited

U.S. PATENT DOCUMENTS

| 5,639,275 | A | * | 6/1997 | Baetge et al. | ............ | 604/891.1 |
| 6,143,530 | A | | 11/2000 | Crouzet et al. | | |
| 6,153,432 | A | | 11/2000 | Halvorsen et al. | | |
| 7,015,037 | B1 | * | 3/2006 | Furcht et al. | ................ | 435/372 |
| 2001/0014319 | A1 | | 8/2001 | Denefle et al. | | |
| 2002/0076395 | A1 | * | 6/2002 | Crystal et al. | ............... | 424/93.2 |
| 2002/0177551 | A1 | | 11/2002 | Terman | | |
| 2004/0092011 | A1 | | 5/2004 | Wilkison et al. | | |
| 2005/0008621 | A1 | * | 1/2005 | Kirkland et al. | .......... | 424/93.21 |

FOREIGN PATENT DOCUMENTS

| EP | 0 237 966 | A2 | 9/1987 |
| EP | 0 237 966 | A3 | 9/1987 |
| EP | 0 281 822 | A2 | 9/1988 |
| EP | 0 281 822 | A3 | 9/1988 |
| EP | 0 326 907 | A1 | 8/1989 |
| EP | 0 394 951 | A1 | 10/1990 |
| EP | 0 493 737 | A1 | 7/1992 |
| GB | 2327224 | A | 1/1999 |
| JP | 11-500618 | A | 1/1999 |
| JP | 11-501518 | A | 2/1999 |
| JP | 11-127870 | | 5/1999 |
| JP | 2001-521740 | A | 11/2001 |
| WO | WO 86/07595 | A1 | 12/1986 |
| WO | WO 87/01728 | A1 | 3/1987 |
| WO | WO 87/03885 | A1 | 7/1987 |
| WO | WO 89/04832 | A1 | 6/1989 |
| WO | WO 97/49827 | A2 | 12/1997 |
| WO | WO 97/49827 | A3 | 12/1997 |
| WO | WO99/11786 | A1 | 3/1999 |
| WO | WO99/23216 | A2 | 5/1999 |
| WO | WO99/61642 | A1 | 12/1999 |
| WO | WO 00/31267 | A1 | 6/2000 |
| WO | WO 01/11011 | A2 | 2/2001 |
| WO | WO 02/06450 | * | 1/2002 |

OTHER PUBLICATIONS

Hertzel et al. J. Lipid Res. 41:1082-1086; 2000.*
Zhang et al. J. Endocrinol. 164:119-128; 2000.*
Komarcevic, Aleksandar; "Modern approach to Wound Management (translated)";*Med. Pregl*; Jul.-Aug. 2000; pp. 363-368; vol. LIII, No. 7-8; (with English Summary).
Abraham, Judith A. et al., "Human basic fibroblast growth factor: nucleotide sequence and genomic organization," *The EMBO Journal* 5(10):2523-2528 (1986).
Abumrad, Nada A. et al., "Cloning of a rat adipocyte membrane protein implicated in binding or transport of long-chain fatty acids that is Induced during preadipocyte differentiation," *The Journal of Biological Chemistry* 268(24):17665-17668 (Aug. 25, 1993).

(Continued)

*Primary Examiner*—Fereydoun G Sajjadi
(74) *Attorney, Agent, or Firm*—Townsend and Townsend and Crew LLP

(57) ABSTRACT

The present invention relates to primary cultured adipocytes for gene therapy, where the adipocytes stably maintain a foreign gene encoding a protein that is secreted outside of cells. This invention provides cells suitable for gene therapy, which can replace bone marrow cells and liver cells used for conventional ex vivo gene therapy. The present invention established methods for transferring foreign genes into primary cultured adipocytes, which are suitable for ex vivo gene therapy; can be easily collected and implanted; and can be removed after implantation. Specifically, the present invention established these methods that use retroviral vectors. The present invention also established primary cultured adipocytes for gene therapy, where the adipocytes stably maintain a foreign gene encoding a protein that is secreted outside of cells.

13 Claims, 16 Drawing Sheets

OTHER PUBLICATIONS

Arai, Tohru et al., "A new system for stringent, high-titer vesicular stomatitis virus G proteln-pseudotyped retrovirus vector induction by Introduction of Cre recombinase into stable prepackaging cell lines," *Journal of Virology* 72(2):1115-1121 (Feb. 1998).

Bradley, Richard L. et al., "The adipocyte as a secretory organ: Mechanisms of vesicle transport and secretory pathways," *Recent Prog. Horm. Res.* 56:329-358 (2001).

Burns, Jane C. et al., "Vesicular stomatitis virus G glycoprotein pseudotyped retroviral vectors: Concentration to very high titer and efficient gene transfer into mammalian and nonmammalian cells," *Proc. Natl. Acad. Sci. U.S.A.* 90:8033-8037 (Sep. 1993).

Byun, J. et al., "A simple and rapid method for the determination of recombinant retrovirus titer by G418 selection," *Gene Therapy* 3:1018-1020 (1996).

Cashion, L.M. et al., "Use of enhanced green fluorescent protein to optimize and quantitate infection of target cells with recombinant retroviruses," *BioTechnigues* 26(5):924-930 (May 1999).

Challita, Pia-Maria and Donald B. Kohn, "Lack of expression from a retroviral vector after transduction of murine hematopoletic stem cells is associated with methylation in vivo," *Proc. Natl. Acad. Sci, U.S.A.* 91:2567-2571 (Mar. 1994).

Chen, Hui et al., "Protein-tyrosine phosphatases PTP1B and Syp are modulators of insulin-stimulated translocation of GLUT4 in transfected rat adipose cells," *The Journal of Biological Chemistry* 272(12):8026-8031 (Mar. 21, 1997).

Chen, Wen Yong et al., "Reactivation of silenced, virally transduced genes by inhibitors of histone deacetylase," *Proc. Natl, Acad. Sci. U.S.A.* 94:5798-5803 (May 1997).

Chen, Wen Yong and Tim M. Townes, "Molecular mechanism for silencing virally transduced genes involves histone deacetylation and chromatin condensation," *PNAS* 97(1):377-382 (Jan. 4, 2000).

Christensen, Rikke et al., "Cutaneous gene therapy—an update," *Histochem. Cell Biol.* 115(1):73-82 (Jan. 2001).

Claudio, Pier Paolo et al., "Application of the primer in situ DNA synthesis (PRINS) technique to titer recombinant virus and evaluation of the efficiency of viral transduction," *Analytical Biochemistry* 291:96-101 (2001).

Dillon, Joseph S. et al., "Cloning and functional expression of the human glucagon-like peptide-1 (GLP-1) receptor," *Endocrinology* 133(4):1907-1910 (1993).

Drucker, Daniel J., "Glucagon-like peptides," *Diabetes* 47:159-169 (Feb. 1998).

Drucker, Daniel J., "Development of glucagons-like peptide-1-based pharmaceuticals as therapeutic agents for the treatment of diabetes," *Current Pharmaceutical Design* 7:1399-1412 (2001).

Drucker, Daniel J., "Minireview: the glucagon-like peptides," *Endocrinology* 142(2):521-527 (2001).

Drucker, Daniel J., "Biological actions and therapeutic potential of the glucagons-like peptides," *Gastroenterology* 122:531-544 (2002).

Drucker, Daniel J. et al., "Glucagon-like peptide I stimulates insulin gene expression and increases cyclic AMP levels in a rat islet cell line," *Proc. Natl. Acad Sci. U.S.A.* 84:3434-3438 (May 1987).

Emi, Nobuhiko et al., "Pseudotype formation of murine leukemia virus with the G protein of vesicular stomatitis virus," *Journal of Virology* 65(3):1202-1207 (Mar. 1991).

GenBank Accession No. K02729, "Mouse leukemia virus (amphotropic)", Aug. 1, 2002 http://www.ncbl.nlm.nih.gov/entrez.

GenBank Accession No. NP_002053, "glucagon-like peptide 1 receptor [*Homo sapiens*]", Apr. 23, 2005 http://www.ncbi.nlm.nih.gov/entrez.

Goto, Masaki et al., "Inhibitory effect of E3330, a novel quinine derivative able to suppress tumor necrosis factor-α generation, on activation of nuclear factor-κB," *Molecular Pharmacology* 49:860-873 (1996).

Graziano, Michael P. et al., "Cloning and functional expression of a human glucagon-like peptide-1 receptor," *Biochemical and Biophysical Research Communications* 196(1):141-146 (Oct. 15, 1993).

Groskreutz, Debyra J. et al., "Genetically engineered proinsulin constitutively processed and secreted as mature, active insulin," *The Journal of Biological Chemistry* 269(8):6241-6245 (Feb. 25, 1994).

Hauner, Hans et al., "Promoting effect of glucocorticoids on the differentiation of human adlpocyte precursor cells cultured in a chemically defined medium," *J. Clin. Invest.* 84:1663-1670 (Nov. 1989).

Hertzel, Ann Vogel et al., "Adenovirus-mediated gene transfer in primary murine adipocytes," *Journal of Lipid Research* 41:1082-1086 (2000).

Hoeben, Rob C. et al., "Inactivation of the Moloney murine leukemia virus long terminal repeat in murine fibroblast cell lines is associated with methylation and dependent on its chromosomal position," *Journal of Virology* 65(2):904-912 (Feb. 1991).

Jahner, Detlev and Rudolf Jaenisch, "Retrovirus-induced de novo methylation of flanking host sequences correlates with gene inactivity," *Nature* 315:594-597 (Jun. 13, 1985).

Johnston, James and Christopher Power, "Productive infection of human peripheral blood mononuclear cells by feline Immunodeficiency virus: Implications for vector development," *Journal of Virology* 73(3):2491-2498 (Mar. 1999).

Johnston, Julie C. et al., "Minimum requirements for efficient transduction of dividing and nondividing cells by feline Immunodeficiency virus vectors," *Journal of Virology* 73(6):4991-5000 (Jun. 1999).

Kaplitt, Michael G. et al., "Long-term gene expression and phenotypic correction using adeno-associated virus vectors in the mammalian brain," *Nature Genetics* 8:148-154 (Oct. 1994).

Kay, Mark A. et al., "Viral vectors for gene therapy: the art of turning infectious agents into vehicles of therapeutics," *Nature Medicine* 7(1):33-40 (Jan. 2001).

Kessler, Paul D. et al., "Gene delivery to skeletal muscle results in sustained expression and systemic delivery of a therapeutic protein," *Proc. Natl. Acad. Sci. U.S.A.* 93:14082-14087 (Nov. 1996).

Kim, V. Narry et al.. "Minimal requirement for a lentivirus vector based on human immunodeficiency virus type 1," *Journal of Virology* 72(1):811-816 (Jan. 1998).

Kreymann, B. et al., "Glucagon-like peptide-1 7-36: A physiological incretin in man," *The Lancet* 2(8571):1300-1304 (Dec. 5, 1987).

Lee, Hyun Chul et al., "Remission in models of type 1 diabetes by gene therapy using a single-chain insulin analogue," *Nature* 408:483-488 (Nov. 23, 2000).

Lund, Anders H. et al., "Transcriptional silencing of retroviral vectors," *J. Biomed. Sci.* 3:365-378 (1996).

Marko, Olga et al., "Isolation of a preadipocyte cell line from rat bone marrow and differentiation to adipocytes," *Endocrinology* 136(10):4582-4588 (1995).

Meier, Juris J. et al., "Glucagon-like peptide 1 as a regulator of food Intake and body weight: therapeutic perspectives," *European Journal of Pharmacology* 440:269-279 (2002).

Mick, Gail G. et al., "White adipocyte vascular endothelial growth factor: regulation by insulin" *Endocrinology* 143(3):948-953 (2002).

Miyao, Yasuyoshi et al., "A simplified general method for determination of recombinant retrovirus titers," *Cell Structure and Function* 20:177-183 (1995).

Mojsov, Svetlana et al., "Insulinotropin: Glucagon-like peptide I (7-37) co-encoded in the glucagon gene is a potent stimulator of insulin release in the perfused rat pancreas," *J. Clin. Invest.* 79:616-619 (Feb. 1987).

Morgenstern, Jay P. and Harmut Land, "Advanced mammalian gene transfer: high titre retroviral vectors with multiple drug selection markers and a complementary helper-free packaging cell line," *Nucleic Acids Research* 18(12):3587-3596 (1990).

Muzyczka, N., "Use of adeno-associated virus as a general transduction vector for mammalian cells," *Current Topics in Microbiology and Immunology* 158:97-129 (1992).

Prats, Herve et al., "High molecular mass forms of basic fibroblast growth factor are Initiated by alternative CUG codons," *Proc. Natl. Acad. Sci. U.S.A.* 86:1836-1840 (Mar. 1989).

Naldini, Luigi et al., "In vivo gene delivery and stable transduction of nondividing cells by a lentiviral vector," *Science* 272:263-267 (Apr. 12, 1996).

Niwa, Ohtsura et al., "Independent mechanisms involved in suppression of the Moloney leukemia virus genome during differentiation of murine teratocarcinoma cells," *Cell* 3:1105-1113 (Apr. 1983).

Poeschla, Eric et al., "Development of HIV vectors for anti-HIV gene therapy," *Proc. Natl. Acad. Sci. U.S.A.* 93:11395-11399 (Oct. 1996).

Poeschla, Eric M. et al., "Efficient transduction of nondividing human cells by feline immunodeficiency virus lentiviral vectors," *Nature Medicine* 4(3):354-357 (Mar. 1998).

Prats, Herve et al., "High molecular mass forms of basic fibroblast growth factor are Initiated by alternative CUG odons," *Proc. Natl. Acad. Sci. U.S.A.* 86:1836-1840 (Mar. 1989).

Raper, S.E. and J.M. Wilson, "Cell transplantation in liver-directed gene therapy," *Cell Transplant.* 2(5):381-400 (Sep.-Oct. 1993).

Rose. John K. and Carol J. Gallione, "Nucleotide sequences of the mRNA's encoding the vesicular stomatitis virus G and M proteins determined from cDNA clones containing the complete coding regions," *Journal of Virology* 39(2):519-528 (Aug. 1981).

Russell, David W. and A. Dusty Miller, "Foamy virus vectors," *Journal of Virology* 70(1):217-222 (Jan. 1996).

Shinnick, Thomas M. et al., "Nucleotide sequence of Moloney murine leukaemia virus," *Nature* 293:543-548 (Oct. 15, 1981).

Sorge, Joe et al., "Amphotropic retrovirus vector system for human cell gene transfer," *Molecular and Cellular Biology* 4(9):1730-1737 (Sep. 1984).

Spirito, Flavia et al., "Cutaneous gene transfer and therapy: the present and the future," *J. Gene Med.* 3:21-31 (2001).

Srinivasakumar, Narasimhachar at al., "The effect of viral regulatory protein expression on gene delivery by human immunodeficiency virus type 1 vectors produced in stable packaging cell lines," *Journal of Virology* 71(8):5841-5848 (Aug. 1997).

Stoffel, Markus et al., "Human glucagon-like peptide-1 receptor gene: Localization to chromosome band 6p21 by fluorescence in situ hybridization and linkage of a highly polymorphic simple tandem repeat DNA polymorphism to other markers on chromosome 6," *Diabetes* 42:1215-1218 (1993).

Sugihara, Hajime et al.; "Primary cultures of unilocular fat cells: Characteristics of growth in vitro and changes in differentiation properties," *Differentiation* 31:42-49 (1986).

Sugihara, Hajime et al., "Proliferation of unilocular fat cells in the primary culture," *Journal of Lipid Research* 28:1038-1045 (1987).

Sugihara et al., "Proliferation and differentiation of fat cells," *Nippon Rinsho* 53(Suppl):115-120 (1995).

Tafuro, S. et al., "Rapid retrovirus titration using competitive polymerase chain reaction," *Gene Therapy* 3:679-684 (1996).

Tani, K. et al., "Gene therapy using hematopoletic cells (Translation)," *Saishin Igaku* 56(2):258-267 (2001).

Thorens, Bernard et al., "Cloning and functional expression of the human Islet GLP-1 receptor: Demonstration that exendin-4 is an agonist and exendin-(9-39) an antagonist of the receptor," *Diabetes* 42:1678-1682 (1993).

Thyagarajan, Bhaskar et al., "Site-specific genomic Integration in mammalian cells mediated by phage φC31 Integrase," *Molecular and Caviar Biology* 21(12):3926-3934 (Jun. 2001).

Toyooka et al., "Gene therapy: It's present status and future direction (Translation)," *Folia Phannacol. Jpn.* 116:158-162 (2000).

Wu, Min and Ayalew Mergia, "Packaging cell lines for simian foamy virus type 1 vectors," *Journal of Virology* 73(5):4498-4501 (May 1999).

Xiao, Weidong et al., "Adeno-associated virus as a vector for liver-directed gene therapy," *Journal of Virology* 72(12):10222-10226 (Dec. 1998).

Xiao, Xiao et al., "Efficient long-term gene transfer into muscle tissue of immunocompetent mice by adeno-associated virus vector" *Journal of Virology* 70(11):8098-8108 (Nov. 1996).

Yee, Jiing-Kuan et al., "Gene expression from transcriptionally disabled retroviral vectors," *Proc. Natl. Acad. Sci. U.S.A.* 84:5197-5201 (Aug. 1987).

Yee. Jiing-Kuan et al., "Generation of high-titer pseudotyped retroviral vectors with very broad host range," *Methods in Cell Biology* 43:99-112 (1994).

Yu, Sheau-Fung et al., "Self-inactivating retroviral vectors designed for transfer of whole genes into mammalian cells," *Proc. Natl. Acad. Sci. U.S.A.* 83:3194-3198 (May 1986).

Zhang, H. H. et al., "Ceiling culture of mature human adipocytes: use in studies of adipocyte functions," *Journal of Endocrinology* 164:119-128 (2000).

Zufferey, Romain et al., "Multiply attenuated lentiviral vector achieves efficient gene delivery in vivo," *Nature Biotechnology* 15:871-875 (Sep. 1997).

Zufferey, Romain et al., "Self-inactivating lentivirus vector for safe and efficient in vivo gene delivery," *Journal of Virology* 72(12):9873-9880 (Dec. 1998).

Levine, James A., et al.; "Adenoviral-Mediated Gene Transfer to Human Adipocytes in Vitro, and Human Adipose Tissue Ex Vivo and Rabbit Femoral Adipose Tissue In Vivo;" *J. Nutr. Sci. Vitaminol*; 1998; pp. 569-572; vol. 44, No. 4.

Ito, M., et al.; "Implantation of primary cultured adipocytes that secrete insulin modifies blood glucose levels in diabetic mice;" *Diabetologia*; pp. 1614-1620; 48:8.

Shibasaki, M., et al.; "Alterations of insulin sensitivity by the implantation of 3T3-L1 cells in nude mice. A role for TNF-α?;" *Diabetologia*; Apr. 2002; pp. 518-526; 45:4.

Simonson, Gregg D., et al.; "Synthesis and Processing of Genetically Modified Human Proinsulin by Rat Myoblast Primary Cultures;" *Human Gene Therapy*; Jan. 1, 1996; pp. 71-78; 7:1.

Bestor, Timothy J., "Gene silencing as a threat to the success of gene therapy," 2000, *J. Clin. Invest.*, vol. 105(4), pp. 409-411.

Hirai, Y., et al., "Development of a method of adeno-associated virus (AAV) vector-mediated gene transfer," 1994, *Jikken-iqaku Zokan*, vol. 12(15), pp. 41-16.

Hirai, Y., et al., Chapter 2 Method for preparing viral vectors; (3) Method for preparing adeno-associated virus vectors,: 1996, *Jikken-iqaku Bessatsu*, vol. 51, pp. 111-126.

Jackson, L., et al., "Adult mesenchymal stem cells; Differentiation potential and therapeutic applications," 2007, *J. Postrgrad Med.*, vol. 53(2), pp. 121-127. (larger version of Figure 1 included).

Feuerbach et al.; "Progress in human gene therapy"; *Kidney Int.*; 49(6):1791-4 (Jun. 1996).

Roman, et al., "Circulating Human or Canine Factor IX from Retrovirally Transduced Primary Myoblasts and Established Myoblast Cell Lines Grafted into Murine Skeletal Muscle," *Somatic Cell and Molecular Genetics*, vol. 18, No. 3, 1992, pp. 247-258.

Yokoyama et al., "Autologous Primary Muscle-Derived Cells Transfer into the Lower Urinary Tract," *Tissue Engineering*, vol. 7, No. 4, 2001, pp. 395-404.

\* cited by examiner (A)

(B)

(C)

(D)

(A)

(B)

(A)

(B)

(C)

PRIMARY CULTURED ADIPOCYTES FOR GENE THERAPY

TECHNICAL FIELD

The present invention relates to primary cultured adipocytes for gene therapy, to which a foreign gene(s) has been transferred.

BACKGROUND ART

Current gene therapies (Toyooka et al., Folia Pharmacol. Jpn. 116:158-162, 2000) can be classified into two groups: (1) methods of transferring therapeutic genes into patients by directly administering viral vectors, naked plasmids, or such that encode the gene (in vivo), and (2) methods of temporarily removing cells from patients, transferring a gene to these cells, and then returning these cells to the patient (ex vivo). In the in vivo methods, major problems remain to be solved, such as transfer efficiency, continuous expression, and selective gene transfer to target cells. Ex vivo methods, on the other hand, can potentially overcome these problems. The majority of examples of ex vivo methods have been performed using blood-system cells (peripheral lymphocytes and bone marrow cells), since their collection and transplantation is relatively easy and the burden on patients is reduced (Tani et al., Saishin Igaku, 56:258-267, 2001). With regards to cells other than blood-system cells, methods that transfer genes to hepatocytes and then return these cells to the patient have been carried out (Raper, S. E. et al., Cell Transplant 2(5):381-400, 1993), but most of these methods focus on the recovery, maintenance, and enhancement of the function of the transfected cells themselves.

DISCLOSURE OF THE INVENTION

While searching for cells suitable for ex vivo gene therapy, the present inventors developed the idea of using primary cultured adipocytes. The use of adipocytes has the following advantages:

(1) there are many reports of humoral factors secreted from adipocytes, and adipocytes comprise the functions of hormone production and can act as secretary organs (Bradley R. D., et al., Recent Prog. Horm. Res., 2001, 56, 329-358);

(2) adipocytes can be easily collected since they also exist subcutaneously, and techniques relating to their extirpation are being developed in the fields of plastic and cosmetic surgery; furthermore, even when adipocytes are grafted to subcutaneous tissue, which allows easy implantation, these cells are not heterotropic since they originally belonged to this region;

(3) since isolated primary cultured adipocytes actively proliferate, even in vitro, they are appropriate for procedures such as gene transfer;

(4) since adipocytes are likely to stay in a limited area after implantation, the grafted cells can be extirpated after implantation if so desired (specifically, when wanting to eliminate the gene expression);

(5) since adipocytes themselves produce angiogenetic factors (Mick, G. J., et al., Endocrinology 2002, 143(3):948-53), a high level of engraftment can be expected after implantation;

(6) adipocyte extirpation or implantation has a small impact on the human body because the weight of this organ changes greatly in adults; and (7) adipocytes are widely recognized as superfluous and obstructive, and consent for their collection may be obtained easily.

Although investigations with similar objectives are currently underway using keratinocytes (J. Gene. Med. 2001 January-February, 3(1): 21-31; Histochem. Cell Biol. 2001 January, 115(1):73-82), removing the biological barrier of the skin in the process of isolating the primary culture is problematic considering infection risk. Patient pain during extirpation and implantation is predicted to be severe, and re-extirpation (4, mentioned above) to eliminate expression is not easy. Furthermore, when using keratinocytes or skin, which can only be grafted two-dimensionally, the amount of the graft can only be increased by increasing the graft surface area. Therefore, adipocytes, which allow three-dimensional transplantation, are considered more useful.

The present inventors designed methods for efficiently transferring genes into primary cultured adipocytes. They also confirmed that the transferred genes are functioning after implantation, and found that adipocytes can be effectively utilized in gene therapy. Furthermore, adipocytes that stably express the transferred foreign gene in vivo for a long period of time can be obtained by the methods of this invention. The implanted mature adipocytes can continue to express foreign genes for one year or longer. Furthermore, if expression of the foreign gene becomes unnecessary after adipocyte implantation, expression can be stopped by removing the graft.

Specifically, the present invention relates to primary cultured adipocytes for gene therapy, which stably hold a foreign gene(s) encoding a protein(s) that is secreted outside of the cell, methods of producing these cells, implant compositions comprising these cells, the use of these cells, and the like, and more specifically to:

[1] a primary cultured adipocyte for gene therapy, wherein the adipocyte stably maintains a foreign gene encoding a protein that is secreted outside of a cell;

[2] the adipocyte of [1], wherein the gene is transferred to the cell by a retroviral vector or adeno-associated viral vector;

[3] the adipocyte of [1], which his the ability to significantly express the protein in vivo for at least 20 days;

[4] the adipocyte of [1], which is used to release the protein into the blood flow;

[5] the adipocyte of [1], wherein the protein is insulin or glucagon-like peptide 1 (GLP-1);

[6] a method of producing an adipocyte for gene therapy, wherein the method comprises the steps of:

(i) primary culturing an adipocyte; and (ii) transferring, and then stably holding a foreign gene encoding a protein that is secreted outside of the cell;

[7] the method of [6], wherein the foreign gene is transferred by a retroviral vector or adeno-associated viral vector;

[8] an adipocyte for gene therapy, which is produced by the method of [6] or [7];

[9] an implant composition for gene therapy, wherein the composition comprises a primary cultured adipocyte, which stably holds a foreign gene encoding a protein that is secreted outside of the cell, and a pharmaceutically acceptable carrier;

[10] the implant composition of [9], which further comprises an extracellular matrix component;

[11] the implant composition of [9], which further comprises an angiogenesis factor;

[12] a gene therapy method comprising the step of administering a body with a primary cultured adipocyte, which stably holds a foreign gene encoding a desired therapeutic protein that is secreted outside of a cell;

[13] a method of releasing a protein into the blood flow, wherein the method comprises the step of administering a body with a primary cultured adipocyte that stably holds a foreign gene encoding a protein that is secreted outside of the cell;

[14] the method of [13], which is a method for releasing the protein into the blood flow for 20 days or more;

[15] a method for lowering blood glucose, wherein the method comprises the step of administering a body with a primary cultured adipocyte, which stably holds a gene encoding insulin or glucagon-like peptide 1 (GLP-1); and

[16] an animal, the body of which is implanted with a primary cultured adipocyte that stably holds a foreign gene that encodes a protein secreted outside of a cell.

Hereinafter, the mode for carrying out this invention will be described.

First, the present invention provides primary cultured adipocytes for gene therapy, where the adipocytes stably maintain a foreign gene(s) encoding a protein(s) that is secreted to the cell exterior.

Herein, a foreign gene refers to a gene transferred into primary cultured adipocytes from the outside, and comprises genes encoding proteins that are not produced by the primary cultured adipocytes. Furthermore, primary cultured cells refer to non-established cells that are cultured from tissues removed from a living body. Adipocytes refer to mature adipocytes and cells comprising the ability to differentiate into adipose tissue, such as preadipocytes. More specifically, unless the adipocytes are particularly said to be "mature" adipocytes, they also include preadipocytes. Mature adipocytes are spherical cells that store fat, and contain lipid droplets. Fat stored in mature adipocytes can be identified using oil red O staining. Mature adipocytes generally secrete leptin in response to insulin. Preadipocytes normally exist as stromal cells that have not yet differentiated into mature adipocytes. Preadipocytes can be isolated by treating adipose tissue with collagenase, or can be isolated as a result of the division of mature adipocytes, using the ceiling culture method described below (Sugihara, et al. Nippon Rinsho 1995, 53, 115-120; Sugihara, H., et al. J. Lipid Res. 1987, 28, 1038-1045; Zhang H. H., et al. J. Endcriniol. 2000, 164, 119-128). Although the existence of adipocyte-specific surface antigens has not been confirmed, high levels of CD36 expression and such have been found in mature adipocytes (Abumrad N. A., et al. J. Biol. Chem. 1993 Aug. 25, 268(24):17665-8). Therefore, extremely pure adipocytes may be collected by using such molecules as markers. By inducing differentiation as described below, preadipocytes can differentiate into mature adipocytes within a few days to few weeks (Hauner H., et al., J. Clin. Invest. 84, 1663-1670, 1989; Marko, et al., Endocrinology 136, 4582-4588, 1994). Primary cultured adipocytes can be isolated from a desired tissue, for example, subcutaneous adipose tissue or visceral adipose tissue such as tissue surrounding the epididymis or mesenteric tissue.

The phrase "for gene therapy" refers to using the in vivo expression of a protein(s) encoded by a foreign gene(s) in anticipation of a therapeutic effect. Furthermore, cells for gene therapy refer to cells carrying a foreign gene(s), in which the cells are used for administering the foreign gene into a body by ex vivo administration, and the cells comprise the ability to express the protein in that body. Ex vivo administration refers to removing adipose tissues or adipocytes from an individual, performing gene transfer in vitro, and then implanting the cells to the same or a different individual.

Cells for gene therapy preferably refer to cells used for treating disorders, which are cells that are implanted so that a specific protein is produced. Preferably, treatment by a specific protein includes replacement therapy, which uses a protein whose physical or functional deficiency or absence causes a disorder; or neutralization therapy, which uses a protein comprising an action that may neutralize factors that cause the onset and aggravation of a certain pathogenesis. Preferably, the specific protein is a protein that shows activity in the bloodstream, or is supplied to a target tissue via the bloodstream, and functions at the cell surface of that tissue. A continuous supply of the specific protein is also preferably required for a certain period of time (for example, for a few days to a few weeks or more). Factors and disorders for which protein replacement therapy is already being carried out, or is predicted to be effective, may all become targets.

Hereinafter, representative targets are listed according to their classification, but their use is not to be understood as being limited to these examples, and the use of similar factors for similar purposes is included within the scope of this invention.

Replacement therapy includes supplementation against disorders that develop or are exacerbated by a lack or reduced function of a hormone or cytokine, supplementation against disorders due to a congenital genetic defect, and supplementation of a factor for pathological improvement:

insulin/diabetes; glucagon-like peptide-1 (GLP-1)/diabetes, obesity, eating disorders; GLP-2/inflammatory enteropathy, gastrointestinal disorders accompanying cancer chemotherapy; leptin/obesity, lipodystrophic diabetes; adiponectin/diabetes, angiopathy; blood coagulation factors VIII and IX/hemophilia; lipoprotein lipase (LPL)/LPL deficiency, hypertriglyceridemia; lecithin cholesterol acyltransferase (LCAT)/LCAT-deficiency; erythropoietin/erythropenia; apo A-I/hypo-HDL cholesterolemia; albumin/hypoproteinemia; atrial natriuretic peptide (ANP)/hypertension, cardiac failure; luteinizing hormone releasing hormone (LHRH)/breast cancer, prostate cancer; angiostatin, endostatin/angiogenesis, metastasis inhibition; morphine receptor agonist peptide (endogenous opioid peptide (e.g., enkephalin), dynorphin, etc.)/pain relief; calcitonin and bone morphogenetic factor (BMP)/osteoporosis; interferon-α and -β/malignant tumor; interferon-γ/malignant tumor, hepatitis, allergy; interferon-β1/multiple sclerosis; interleukin-1α and -1β/malignant tumor; interleukin-4/psoriasis; interleukin-10/autoimmune disease; interleukin-12/malignant tumor; pancreatic secretory trypsin inhibitor/pancreatitis; superoxide dismutase/ischemic heart disease, angiopathy; and such.

Neutralization therapies against pathologic formation factors or malignant transformation factors include the production of partial peptides of solubilized receptors or neutralizing antibodies, or dominant negative proteins.

tumor necrosis factor-α (TNF-α) solubilized receptor/rheumatoid arthritis; solubilized IgE receptor/allergies; solubilized IgA receptor/food allergies; solubilized cytotoxic T lymphocyte antigen-4 (CTLA4)/autoimmune diseases; solubilized CD40 ligand/immunological disorders; dominant negative blood coagulation factor VIIa/thrombosis; fibroblast growth factor (FGF) solubilized receptor/vascular intimal thickening, and so on.

Furthermore, the adipocytes of the present invention are not limited to those used for so-called "therapy", but include cells used for in vivo expression of a desired secretory protein. For example, the methods of this invention enable production of model animals by a posteriori expression of a particular protein. Using these methods, disease model animals with a posteriori expression of pathogenesis or aggravative factors can be produced, and these animals can be used to screen drugs. Furthermore, by expressing pathologic improvement factors, these methods can be utilized as proof of working hypotheses for novel drug discoveries in which a given factor improves a pathologic condition. The animals that are used include desired non-human animals, and preferably non-human mammals (including rodents and primates).

The primary cultured adipocytes for the gene therapies of this invention stably maintain a foreign gene(s) that encodes a protein(s) that is secreted outside of the cell. The phrase "stably maintains" means that the foreign gene is passed on to daughter cells during cell division, and more specifically, this phrase refers to the incorporation of the foreign gene into a cell chromosome. The adipocytes for gene therapy of this invention preferably comprise a foreign gene(s), stably transferred by a chromosome-incorporating viral vector. More preferably, the foreign gene is transferred by a retroviral vector.

The retroviral vector is stably integrated into a cell chromosome and comprises the ability to express a transferred gene for a long period. The vector's transfer efficiency and continuation of expression of the transferred gene depends on the cell type. For example, a gene transferred by a retroviral vector can show continued expression while the cells are growing, but expression may stop when cell growth stops (Lund, A. H., et al., J. Biomed. Sci. 1996, 3:365-378; Niwa, O. et al., 1983, Cell, 32:1105-1113). Foreign gene expression is often observed to be suppressed, particularly after introducing the gene into a body by in vivo or ex vivo methods. Such suppression of expression is said to involve de novo methylation of the promoter or coding sequence of the transferred gene (Jahner, D. and Jaenisch, R., Nature 315:594-597, 1985; Challita, P. -M. and Kohn, D. B., Proc. Natl. Acad. Sci. USA 91:2567-2571, 1994; Hoeben, R. C. et al., J. Virol. 65:904-912, 1991). Furthermore, deacetylation of histone is involved in silencing the transferred gene (Chen, W. Y. et al., Proc. Natl. Acad. Sci. USA 97:377-382, 2000; Chen, W. Y. et al., Proc. Natl. Acad. Sci. USA 94:5798-5803, 1997). However, when the present inventors transferred a foreign gene into primary cultured adipocytes using a retroviral vector, surprisingly, expression of the transferred gene was found to persist extremely stably, both in vitro and in vivo. Expression of transferred genes is stable in adipocytes before differentiation and also in mature adipocytes. Expression of the transferred gene was confirmed to persist for the entire duration of the experiment for in vitro cultures (80 days or more), and for the entire duration of the experiment when implanted into the body (360 days or more). Therefore, primary cultured adipocytes, to which a foreign gene(s) has been stably transferred, can be used as implants that stably express a gene(s) for a long period.

The adipocytes for gene therapy of this invention comprise the ability to significantly express a protein(s) encoded by a foreign gene(s) for at least 20 days or more in vitro, or more preferably in vivo. The phrase "significantly express" means, for example, expression is detected at a statistically significant level compared to when the foreign gene is not transferred (for example, with a significance level of 5% or a higher significance). More preferably, the adipocytes of the present invention, when transplanted into a body, comprise the ability to significantly express a protein(s) encoded by a foreign gene (s) in the body for at least 30 days or more, preferably 40 days or more, more preferably 50 days or more, even more preferably 60 days or more, still more preferably 80 days or more, yet even more preferably 100 days or more, yet even more preferably 150 days or more, yet even more preferably 200 days or more, yet even more preferably 250 days or more, yet even more preferably 300 days or more, and yet even more preferably 350 days or more.

The adipocytes for gene therapy of this invention are particularly useful as cells for releasing proteins, that are encoded by foreign genes carried by the cells, into the blood flow. The proteins released into the blood flow include desired secretory proteins that demonstrate activity in the blood stream or at the surface of cells of target tissues, and examples include desired humoral factors such as hormones and cytokines, and antibodies. More specific examples are, as mentioned above, hypoglycemic hormones such as insulin and/or glucagon-like peptide-1 (GLP-1) for treating diabetes and such; blood coagulation factors for treating hemophilia and such; and solubilized fragments of TNF-α receptor or anti-TNF-α antibody (including antibody fragments that comprise an antibody variable region, such as Fab and scFv) in the treatment of diseases exhibiting enhanced TNF-α levels, such as rheumatoid arthritis. For example, for insulin, the cleavage sites (site 1 and site 2) can be substituted with the cleavage sequence of a protease expressed in adipocytes, so that mature insulin can be efficiently produced (for example, Groskreutz, D. J., et al. JBC, 1994, 269(8), 6241). An insulin analogue modified to a single chain may also be used (Lee, H. C., et al., Nature. 2000 Nov. 23, 408(6811):483-8). For GLP-1, a desired peptide that acts as a ligand for the GLP-1 receptor may be used (NP_002053; Thorens, B. et al., Diabetes 42, 1678-1682 (1993); Dillon, J. S. et al., Endocrinology 133, 1907-1910 (1993); Graziano, M. P. et al., Biochem. Biophys. Res. Commun. 196, 141-146 (1993); Stoffel, M. et al., Diabetes 42, 1215-1218 (1993)). An example is GLP-1(7-37) (Diabetes, 1998, 47:159-69; Endocrinology, 2001, 142: 521-7; Curr. Pharm. Des., 2001, 7:1399-412; Gastroenterology, 2002, 122:531-44).

The present invention also relates to methods of producing adipocytes for gene therapy, where the methods comprise the steps of:
(1) primary culturing adipocytes, and
(2) transferring cells with a foreign gene(s) that encodes a protein(s) that is secreted to the cell exterior, preferably using a retroviral vector or an adeno-associated viral vector, so that the gene is stably maintained.

The present invention also relates to the adipocytes for gene therapy produced by this method. "Stably maintained" means transfer of a foreign gene(s) such that it is passed on to daughter cells when the cell divides, and more specifically, it refers to integration of the foreign gene into the chromosome of the cells. Southern blotting or PCR using genomic DNA can molecular biologically -demonstrate that the foreign gene has achieved stable expression by integrating into a chromosome. Furthermore, to concentrate the stably transfected cells, for example, a method using fluorescence activated cell sorting (FACS), which concentrates cells by recognizing the GFP coexpressed by the cells along with the target gene, may be used.

1. Methods of Collecting Primary Cultured Adipocytes

Primary cultured adipocytes can be collected by methods described in the report by Sugihara et al. (Sugihara, H. et al., Differentiation, 31:42-49, 1986). More specifically, adipose tissue, and preferably the implant recipient's own subcutaneous adipose tissue or visceral adipose tissue, such as tissue surrounding the epididymis or mesenteric tissue, is extirpated under sterile conditions, and for example, after washing with PBS, is morcellated using a pair of scissors or a surgical knife. This morcellated tissue is digested by shaking at 37° C. in a medium comprising an appropriate amount of collagenase, preferably 1 to 3 mg/mL, for an appropriate length of time, preferably for 20 to 60 minutes, and then separated into a precipitated residue and floating layer by centrifugation.

The floating layer is preferably further washed once or twice by centrifugation, and is then added to a culture flask filled with medium. Bubbles are removed, and the flask is left to stand in a $CO_2$ incubator for culturing, such that the conventional culture surface is a ceiling (ceiling culture). After culturing for an appropriate period, preferably ten to 14 days, cells adhered to the ceiling surface are collected by trypsin treatment. These cells are subsequently subcultured in a conventional culturing system.

Primary cultured adipocytes may be stored by freezing before or after gene transfer. This procedure allows multiple use of adipocytes after a single collection.

2. Gene Transfer to Adipocytes

Gene transfer can be performed using gene transfer reagents (Fugene 6, Roche; Lipofectamin, Invitrogen; Cellphect transfection kit (calcium phosphate method), Amersham; etc.), electroporation methods (Chen, H. et al., J. Biol. Chem. 1997, 272(12), 8026-31), or viral vectors (Kay, M. A., et al., Nat. Med. 2001, 7, 33-40). Transfer is preferably performed using viral vectors, and more preferably using retroviral vectors (e.g., Arai, T. et al., J. Virol., 1998, 72, pp 1115-21).

When gene transfer is performed using a plasmid, the plasmid is transfected into adipocytes, and those adipocytes stably maintaining the transferred foreign gene can be selected. Such adipocytes can be selected by, for example, equipping the plasmid encoding the foreign gene with a drug-resistance gene, or by performing the transfection together with a plasmid carrying a drug-resistance gene, and then selecting the transfected cells using this drug. Otherwise, the cells can be obtained by cloning the transfected cells by limiting dilution techniques. Furthermore, when gene transfer is performed using a plasmid, a method of transiently expressing a phage-derived integrase can be used to increase the efficiency of chromosomal insertion (Mol. Cell Biol. 2001 Jun., 21(12):3926-34).

An example of gene transfer into adipocytes using a viral vector is a method using an adeno-associated virus (AAV). AAVs are viruses belonging to the genus *Dependovirus* of the Parvoviridae family, and are characterized by chromosomal integration of the transferred gene. A recombinant AVV vector, in which a foreign gene is integrated, can be produced by integrating the foreign gene between two inverted terminal repeats (ITRs), and expressing the AAV packaging proteins (rep and cap gene products) in the presence of adenovirus E1, E2A, and E4 proteins (Muzyczka, N. (1992) Curr. Top. Microbiol. Immunol. 158, 97-29; Kaplitt, M. G. et al. (1994) Nat. Genet. 8, 148-54; Xiao, X. et al. (1996) J. Virol. 70, 8098-108; Kessler, P. D. et al. (1996) Proc. Natl. Acad. Sci. USA.93, 14082-4087; Xiao, W. et al. (1998) J. Virol. 72, 10222-0226).

In the present invention, the foreign gene is more preferably transferred into adipocytes using a retroviral vector. Retroviruses refer to viruses that belong to the Retroviridae family, and include oncoviruses, foamy viruses (Russell, D. W. and Miller, A. D., J. Virol. 1996, 70:217-222; Wu, M. et al., J. Virol. 1999, 73:4498-4501), and lentiviruses (for example, HIV-1 (Naldini, L. et al., Science 1996, 272:263-267; Poeschla, E. et al., Proc. Natl. Acad. Sci. USA 1996, 93:11395-11399; Srinivasakumar, N. et al., J. Virol. 1997, 71:5841-5848; Zufferey, R., et al., Nat. Biotechnol. 1997, 15:871-875; Kim, V. N., et al., J. Virol. 1998, 72:811-816) and feline immunodeficiency virus (Johnston, J. C. et al., J. Virol. 1999, 73:4991-5000; Johnston, J. and Power, C., J. Virol. 1999, 73:2491-2498; Poeschla, E. M. et al., Nat. Med. 1998, 4:354-357)). A preferable retroviral vector for use in this invention is a Moloney murine leukemia virus (MoMLV) vector (T. M. Shinnick, R. A. Lerner and J. G. Sutcliffe, Nature 293, 543-548, 1981).

The retroviruses may be self-inactivating (SIN) vectors. A SIN vector can be prepared by deleting a portion of the 3' LTR during viral packaging (Yu S. F. et al. (1986) Proc. Natl. Acad. Sci. USA 83:3194; Yee, J. K. et al., 1987, Proc. Natl. Acad. Sci. USA 84:5197-5201; Zufferey, R. et al., 1998, J. Virology, 72, 9873-9880). The foreign gene in the retrovirus can be transcribed by LTR, or it may be expressed from another promoter inside the vector. For example, a constitutive expression promoter such as CMV promoter, EF-1α promoter, or CAG promoter, or a desired inducible promoter may be used. Furthermore, a chimeric promoter, in which a portion of LTR is substituted with another promoter, may be used.

To transfer genes using retroviruses, specifically, a plasmid carrying a gene to be transferred, such as pBabe CL-SEAP-IRES-GFP, is gene-transferred to packaging cells, such as 293-EBNA cells (Invitrogen), using a gene transfer reagent and such. This is then cultured for an appropriate period of time, preferably one to three days, and the produced recombinant viruses in the supernatant are collected. These viruses are then infected into the adipocytes to be transfected.

The retroviral vectors preferably comprise an envelope protein with broad tropism, so that they can infect a wide range of mammalian adipocytes, including those of humans. For example, amphotropic envelope protein may be used (for example 4070A) (Accession K02729; Sorge, J. et al., Mol. Cell. Biol. 4 (9), 1730-1737 (1984)). In the present invention the retrovirus is preferably pseudotyped (Emi, T. Friedmann and J. K. Yee, J. Virol., 65 (3), 1202-1207 (1991); Yee, J. -K. et al. (1994) Methods Cell Biol. 43 43:99-112; Burns, J. C. et al. (1993) Proc. Natl. Acad. Sci. USA 90 90:8033-8037) by vesicular stomatitis virus G protein (VSV-G) (Rose, J. K. and Gallione, C. J., J. Virol. 39 (2), 519-528 (1981)). Pseudotyping by VSV-G enables highly efficient transfer of genes into adipocytes. VSV-G pseudotyped vector can be produced by expressing VSV-G in packaging cells. More specifically, for example, packaging cells that can inducibly express VSV-G may be used favorably (for example, Arai T. et al., J. Virol., 1998: 72, pp 1115-21).

The titer of the produced viruses can be determined by infecting cells with virus solutions that have been stepwise diluted, and counting the number of colonies of infected cells (for details, see Ausubel et al). (Ausubel, F. M. et al. Eds. (1995) Current Protocols in Molecular Biology. (John Wiley & Sons, NY)). Alternatively, the titer can be determined by the method of Byun et al. (Byun, J. et al. (1996) Gene Ther. 33333:1018-1020), Tafuro et al. (Tafuro, S. et al. (1996) Gene Ther. 33333:679-684), Miyao et al. (Miyao, Y. et al. (1995) Cell Struct. Funct. 20 20:177-183), Claudio et al. (Claudio, P. P. et al. (2001) Anal. Biochem. 291: 96-101), or Cashion et al. (Cashion, L. M. et al. (1999) Biotechniques 26 26: 924-930).

Primary cultured adipocytes can be introduced with viral vectors by contacting the vectors to the cells. For example, primary cultured adipocytes are incubated in a culture solution comprising viral vectors. Adipocytes are preferably infected in the form of preadipocytes. Infection efficiency can be increased by adding 0.5 to 8 µg/mL or so of polybrene. Multiplicity of infection (MOI) is not particularly limited, but can be appropriately adjusted within the range of 0.1 to 100. Gene transferred cells can be selected using a marker gene, for example. However, if infection is carried out at an MOI of approximately 2 or more, or preferably approximately 3, 4, 5, or more, the gene can be transferred to most cells, even without selection. The gene-transferred adipocytes can be used for implantation without further treatment, or in certain cases, they can be converted to mature adipocytes by culturing in a medium comprising 3-isobutyl-1-methylxanthine (IBMX), dexamethasone, and insulin. In such cases, since IBMX and dexamethasone are used mainly to activate the adipocyte peroxisome proliferator-activated receptor-γ (PPAR-γ), drugs that directly activate this receptor (for example the thiazolidine derivatives, pioglitazone/Takeda Pharmaceutical Company Limited and rosiglitazone/GlaxoSmithKline) may be added at the same time.

The primary cultured adipocytes of this invention, which carry a desired therapeutic gene, can be implanted into the body of an immunologically matched recipient, thus enabling gene therapy by in vivo expression of the secretory protein encoded by the therapeutic gene. The primary cultured adipocytes to be implanted are preferably cells from the same host as the recipient. The gene therapy methods in which the primary cultured adipocytes of this invention are implanted can be applied by expressing a desired secretory protein in a body, in anticipation of that protein's effects. For example, a disorder can be treated or prevented by implanting the adipocytes of this invention, which maintain a foreign gene(s) encoding a protein (s) comprising a therapeutic or preventive effect against the disorder. Furthermore, the present invention relates to methods of releasing proteins into the blood flow, where the methods comprise the step of administering the primary cultured adipocytes of this invention into a body. Using these methods, the protein encoded by a foreign gene can be significantly secreted into the blood flow for at least 20 days or more, preferably 30 days or more, more preferably 40 days or more, even more preferably 50 days or more, still more preferably 60 days or more, yet even more preferably 80 days or more, yet even more preferably 100 days or more, yet even more preferably 150 days or more, yet even more preferably 200 days or more, yet even more preferably 250 days or more, yet even more preferably 300 days or more, and yet even more preferably 350 days or more. The foreign gene expressed in a body can be detected and/or quantified, for example by immunoassays such as EIA. Removal of the transplanted cells can stop the expression of the administered foreign gene at any time. In certain cases, by transferring an inducible suicide gene (e.g., HSV-tk) to the graft cells, the graft cells can be eliminated by administering ganciclovir, for example.

The present invention also provides implant compositions for gene therapy, where the compositions comprise primary cultured adipocytes that stably hold a foreign gene(s) that encodes a protein(s) secreted to the cell exterior, and pharmaceutically acceptable carriers. Examples of the carriers are physiological saline, phosphate buffer, culture solutions, serums, and body fluids. These may also be combined with a solid or gel support that becomes a scaffold for cells.

The implant compositions of the present invention preferably comprise an extracellular matrix (ECM) component. An extracellular matrix component refers to a component such as a protein or mucopolysaccharide comprised in an insoluble network or fibrous structure accumulated between cells. They may be isolated from organisms or artificially reconstructed. ECM components preferably used in this invention are collagen, fibronectin, vitronectin, laminin, heparan sulfate, proteoglycan, glycosaminoglycan, chondroitin sulfate, hyaluronate, dermatan sulfate, keratin sulfate, elastin, or combinations of two or more of the above. Preferably, these ECM components are formed into a gel and then mixed with adipocytes. ECM gels used in this invention are not particularly limited, as long as at least one or more of the above-mentioned components are comprised, but preferably comprise at least type IV collagen, laminin, and heparan sulfate. Such ECMs include a substrate extracted from Engelbreth-Holm-Swarm mouse tumor (Matrigel®) (Becton Dickinson Labware) (U.S. Pat. No. 4,829,000). The structure of the compositions comprising the ECM component and adipocytes used in the present invention is not particularly limited, and may be, for example, a gel or paste network structure, a fibrous structure, flat (disc) structure, honeycomb structure, and sponge-like structure. ECM components can be gelated according to conventional methods. For example, gelation can be performed by incubating an aqueous solution comprising approximately 0.3 to 0.5% collagen at 37° C. for ten to 30 minutes. Otherwise, ECM components can be gelated using a gelation agent.

Furthermore, the implant compositions of the present invention preferably comprise an angiogenesis factor. The implant compositions of this invention that comprise an angiogenesis factor cause blood vessels to form around them after implantation, and can secrete a foreign protein into the blood flow with higher efficiency. The angiogenesis factors are not particularly limited, as long as they are factors that may induce angiogenesis in vivo, and examples are vascular endothelial cell growth factor (VEGF), basic fibroblast growth factor (bFGF), acidic fibroblast growth factor (aFGF), platelet-derived growth factor, transforming growth factor-β (TGF-β), osteonectin, angiopoietin, and hepatocyte growth factor (HGF). The most preferred example is bFGF. bFGFs, which are also called FGF2, are not only fibroblast growth factors, but also comprise the activity of promoting the growth of various cells such as vascular endothelial cells, cartilage, osteoblasts, and epidermal cells (Abraham et al., EMBO J., 5, 2523-2528, 1986; Prats et al., Proc. Natl. Acad. Sci. USA, 86, 1836-1840, 1989). The bFGFs used in the present invention are not only natural proteins, but may also be produced by genetic engineering by recombinant DNA technology, and modified forms thereof. Examples of bFGFs are those described in WO87/01728, WO89/04832, WO86/07595, WO87/03885, European Patent Application Publication Nos. 237966, 281822, 326907, 394951, and 493737. Alternatively, another expression vector that transiently expresses an angiogenesis factor may be introduced into the adipocytes (see WO97/49827). The main objective of angiogenesis factors used in this manner is to form blood vessels around the transplanted cells, so that the foreign protein can be efficiently secreted into the blood flow from the adipocytes of this invention. Therefore, when using a vector encoding a vascular inducing factor to express that vascular inducing factor from adipocytes, the use of a transient expression vector (more specifically, a vector that is not incorporated into the chromosome) is preferred. When the adipocytes express a vascular inducing factor for a long period, excess amounts of blood vessels form around the implanted adipocytes, which may cause systemic side effects. Therefore, it is preferable that the foreign gene encoding an angiogenesis factor is not stably transferred to the primary cultured adipocytes of this invention.

3. Implantation of Adipocytes

Gene transferred adipocytes are prepared at an appropriate cell concentration, preferably $0.2 \times 10^7$ to $2 \times 10^7$ cells/mL, or $0.2 \times 10^6$ to $5 \times 10^6$ cells/mL when transfected with a retrovirus. They are infused as is into the subcutaneous tissue or adipose tissue, preferably subcutaneous tissue, or by mixing with an effective media, preferably a solution comprising an extracellular matrix such as collagen. Injection into adipose tissue can be performed by making an incision and exposing the adipose tissue. Cells that have terminally differentiated into mature adipocytes will not proliferate after transplantation, and will express the foreign gene for a long period at a constant level. The expression level of a foreign gene in a body that receives an implant is proportional to the number of implanted cells. Therefore, when performing an implantation, a desired expression level can be maintained for a long period in a body receiving an implant by adjusting the amount of adipocytes that are implanted to align with a pre-measured in vitro foreign gene expression level.

BEST MODE FOR CARRYING OUT THE INVENTION

The present invention will be described in detail below with reference to Examples, but it is not to be construed as being limited thereto. All references cited herein are incorporated into this description.

EXAMPLE 1

Primary Culture of Murine Adipocytes

[Methods]

Three-week old male ICR mice or four- to five-week old male C57BL/6 mice (both from Charles River) were anesthetized with diethyl ether, and sacrificed by collection of whole blood from the heart. Next, inguinal subcutaneous fat, or fat surrounding the epididymis, and mesenteric adipose tissue were individually extirpated under sterile conditions. The extirpated tissues were washed with PBS, and then morcellated using a pair of scissors or a surgical knife. This morcellated tissue was digested with shaking at 37° C. for 20 to 60 minutes in normal medium (DMEM-high glucose/SIGMA, 10% FCS) comprising 1 mg/mL of collagenase (S1 fraction/Nitta gelatin), and then separated into precipitate and suspended layer by centrifugation (300 g, five minutes).

The floating layer was further centrifuged once or twice to remove the collagenase by dilution, and then added to a T-25 flask (IWAKI) filled with medium. Bubbles were removed, and this was cultured under a 5% $CO_2$ atmosphere in a $CO_2$ incubator at 37° C. so the conventional culture surface was upside (ceiling culture). Ten to 14 days after culturing, the cells adhering to the ceiling surface were collected by trypsin treatment and transferred to a normal culturing system. Subculturing was then performed at a ratio of 1:3 to 1:10.

To induce differentiation, the medium of cells cultured to confluency in a 6-well plate was transferred to an induction medium (normal medium supplemented with 0.5 mM IBMX, 0.25 µM dexamethasone, and 10 µg/mL insulin). This stimulation was continued for 48 hours. Next, the cells were differentiated in a maturation medium (normal medium supplemented with 10 µg/mL insulin). The maturation medium was exchanged every three days.

Oil red O staining solution was prepared by mixing a stock solution, prepared by mixing 0.3 g of oil red O in 100 mL isopropanol (99%), with distilled water in a 3:2 ratio at the time of use. The cells were washed with PBS and then fixed with 10% neutral formalin solution (WAKO). After washing again with PBS, the cells were stained with oil red O staining solution at room temperature for ten minutes. The cells were washed with PBS again, and then examined by microscope.

[Results]

Figure 1:
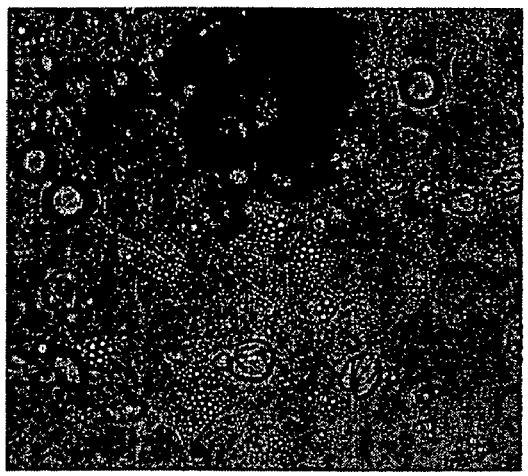
FIG. 1 is a set of microphotographs of primary cultured adipocytes isolated from the subcutaneous fat of three-week old ICR mice. (A) shows adipocytes that adhered to the ceiling-side culture surface after 14 days of ceiling culture, (B) shows primary cultured adipocytes grown in a normal culture, (C) shows mature adipocytes that have stored lipid droplets due to differentiation induction, and (D) shows an oil red O-stained image of differentiation-induced cells.
Figure 1:
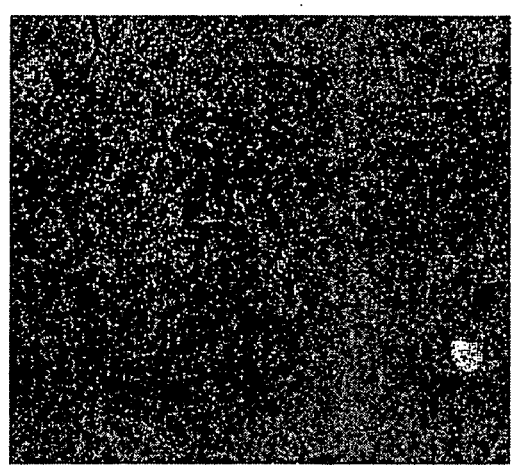
Figure 1:
Figure 1:
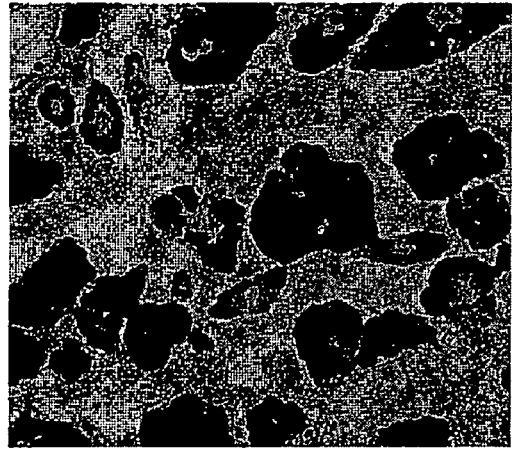

FIG. 1 is a set of microphotographs of primary cultured adipocytes isolated from the subcutaneous fat of three-week old ICR mice. After 14 days of ceiling culture, adhesion of adipocytes carrying lipid droplets was observed on the ceiling-side culture surface (A). When these cells were transferred to a normal culturing system, they showed fibroblast-like growth, as shown in (B). However, when differentiation was induced by IBMX, dexamethasone, and insulin, the cells again differentiated into mature adipocytes that carry lipid droplets (C). Stored fat was stained red with oil red O staining (D). Cells isolated by this method were shown to be primary cultured adipocytes comprising the ability to differentiate.

EXAMPLE 2

Transient transfer of thermostable secretory alkaline phosphatase (AP) gene into primary cultured adipocytes, and implantation of transfected adipocytes into mice As a model system for gene expression, AP gene, more specifically, SEAP gene (Clontech) or PLAP gene (Goto, M. et al. Mol. Pharmacol. vol. 49 860-873 (1996)) was transferred to primary cultured adipocytes, and changes in AP activity were examined. (Both AP gene products are thermostable and can be easily distinguished from endogenous alkaline phosphatases by thermal treatment.)

[Methods]

(1) Production of Primary Cultured Adipocytes Transiently Transfected with the SEAP Gene AP-expressing plasmid (pcDNA3.1-SEAPmh) was constructed by inserting the SEAP sequence, obtained by double digestion of pSEAP2-basic vector (Clontech) with restriction enzymes HindIII-XbaI, into the HindIII-XbaI site of pcDNA3.1Myc-HisA (Invitrogen), which is a vector for expression in mammalian cells.

For every gene transfer to a 10-cm dish, 500 µL of FCS-free DMEM medium and 15 µL of Fugene 6 reagent (Roche) were mixed, then 5 µg of pcDNA3.1-SEAPmh was added. This mixture was left to stand at room temperature for 15 minutes. This mixture was added to primary cultured cells (derived from ICR subcutaneous fat) cultured to 70 to 80% confluency in a 10-cm dish. This was then cultured for 24 hours in a $CO_2$ incubator.

(2) Implanting Mice with Alkaline Phosphatase Gene-transferred Primary Cultured Adipocytes Gene-transferred cells were collected by trypsin treatment, and washed twice with PBS by centrifugation. The cells were then suspended in PBS at $1 \times 10^7$ cells/mL. The animals (ICR nude mice, five-weeks old at the time of operation) were anesthetized by intraperitoneal administration of 50 mg/kg of sodium pentobarbital (Nembutal; Dainippon Pharmaceutical). After disinfecting the area to be operated with dilute Hibitane solution (Sumitomo Pharmaceuticals), a 3 mm to 5 mm or so incision was made to the skin near the base of the right hind leg, and the inguinal subcutaneous fat was exposed. 0.55 mL of the prepared cell suspension solution ($5.5 \times 10^6$ cells/head) was loaded into a 1-mL syringe, and this was injected into the subcutaneous fat using a 22 G injection needle. As a control, PBS was injected to the same site. To compare this to the protein supplementation method, 1 µg of purified AP (Roche) was dissolved in PBS under sterile conditions, and this was injected in a similar manner. The incised skin was sutured and the operated site was disinfected with surgical Isodine (Meiji Seika).

Blood was collected using a heparin-coated capillary (Dramond) from the postorbital venous plexus before implantation (day 0) and after implantation over time. Plasma was obtained from the whole blood by centrifugation at 2000 g for 15 minutes. AP activity in this plasma was measured using an assay kit (SEAP reporter gene assay kit, Roche) by following the attached instructions.

[Results]

Figure 2:
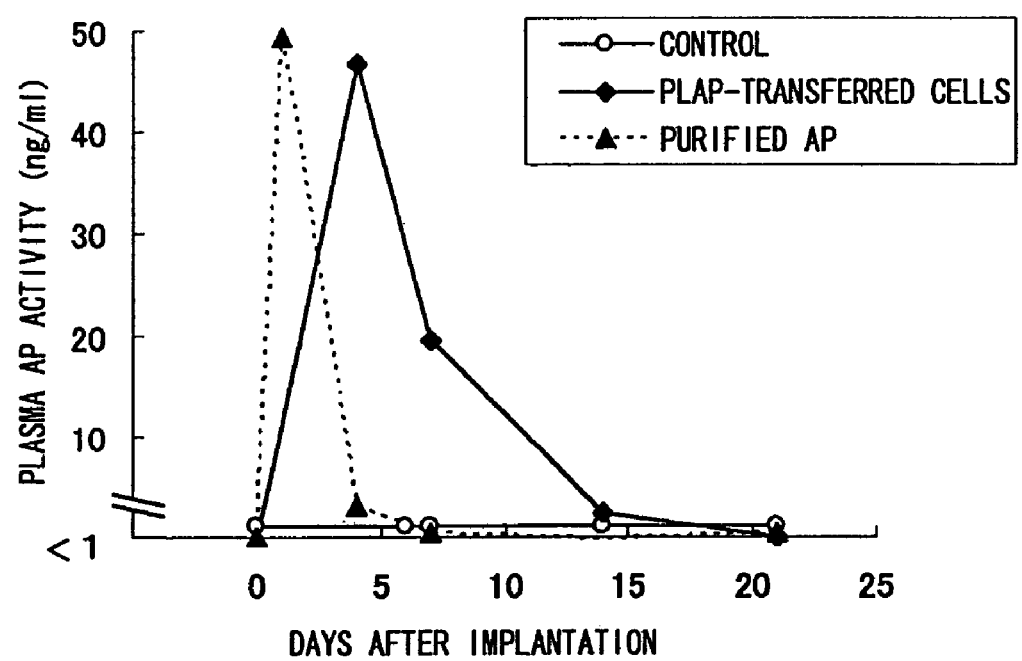
FIG. 2 shows the plasma alkaline phosphatase (AP) activity obtained by implanting ICR nude mice with primary cultured adipocytes (derived from subcutaneous fat of ICR mice) that are transiently transfected with AP-expressing plasmid pcDNA3.1-SEAPmh.

FIG. 2 shows the plasma AP activity achieved by implanting mice with primary cultured cells, which have been transiently transfected with alkaline phosphatase (AP) -expressing plasmid pcDNA3.1-SEAPmh. For purposes of comparison, mice were administered with 1 µg of purified AP protein (Roche) by injection. Seven days after administration the blood AP activity in these mice decreased to the level of the control. On the other hand, blood AP activity in mice that received an implant of cells holding transiently transferred genes was confirmed to peak on the fourth day after implantation, and the duration of expression was 14 days. The duration of in vivo expression by implanting cells carrying transiently transferred gene was short, and the concentration in the blood was found to vary greatly, although it was maintained longer than by injecting protein.

EXAMPLE 3

Production, by Using a Viral Vector, of Adipocytes that Stably Express AP

[Methods]

(1) Construction of AP- and Control GFP-expression Vectors

The PLAP gene was excised from pTK-PLAP using HindIII and BglII, as described in the literature (Goto, M. et al. Mol. Pharmacol. vol.49, 860-873 (1996)). The SEAP gene was obtained by double digestion of pcDNA 3.1-SEAPmh with HindIII/PmeI. The GFP gene was excised from pEGFP-N2 using NotI-NcoI.

The plasmid, pBabeCLXI2G, used for viral vector production, was produced based on pBabePuro (Morgenstern, J. P. et al. Nucleic Acids Res. vol.18, 3587-3596 (1990)), by excising its SV40 promoter and neomycin resistance genes using SalI-ClaI, and blunting those ends with Klenow fragments, then replacing these with the internal ribosome re-entry site (IRES) of encephalomyocarditis virus (EMCV), which was excised from pIRES2-EGFP by HincII-HincII, and the green fluorescent protein (GFP); then replacing the portion from the long terminal repeat (LTR) to the foreign gene insertion site (multicloning site) (SspI-BamHI) with a sequence corresponding (SspI-BamHI) of pCLXSN (IMGENEX). Furthermore, pBabeCLXIP, in which the IRES-GFP portion of pBabeCLXI2G had been replaced with IRES-puromycin resistance gene, was also used.

Each of the DNA fragments of the above-mentioned PLAP, SEAP, and GFP were blunted with Klenow fragments, then inserted into pBabeCLXIP or pBabeCLXI2G vector cleaved with Hpa I, yielding pBabeCL(PLAP)IP, pBabeCL(SEAPmh)I2G, and pBabeCL(GFP)IP, respectively.

(2) Production of Viral Vectors

Each gene transfer to a 10-cm dish was performed as follows: 30 μL of plasmid transfection reagent TransIT (MIRUS) was mixed into 500 μL of FCS-free DMEM medium, and left to stand at room temperature for five minutes (mixed DMEM/TransIT solution). In a separate tube, 3.3 μg of a vector encoding VSV-G (pCALG, modified according to Arai, T. et al., J. Virol., 1998, 72, pp 1115-21), 3.3 μg of a vector encoding Gag-Pol (pCLAmpho/RetroMax system (IMGENEX)), and 3.3 μg of a vector comprising a packaging signal and the transferred gene (pBabeCL(PLAP)IP, pBabeCL(SEAPmh)I2G, or pBabeCL(GFP)IP), were mixed, totaling 9.9 μg (plasmid solution). The plasmid solution was added to the mixed DMEM/TransIT solution, thoroughly mixed, and then left to stand at room temperature for 15 minutes. This was then added to 293-EBNA cells (Invitrogen), cultured overnight from $2 \times 10^6$ cells/10-cm dish on the previous day.

Medium was exchanged eight hours after addition, and the culture supernatant was collected after culturing for another two days. The collected culture supernatant was centrifuged (300 g, five minutes) or filtered through a 0.45 μm syringe filter (Millipore) to remove contaminants, and this supernatant was used as the virus solution (MLV(VSV)/pBabeCL (PLAP)IP, MLV(VSV)/pBabeCL(SEAPmh)I2G, and MLV (VSV)/pBabeCL(GFP) IP, respectively). Some of the virus solution was concentrated by ultracentrifugation (19,500 rpm, 100 minutes) and then used.

(3) Gene Transfer to and Culturing of Primary Cultured Adipocytes

Figure 3:
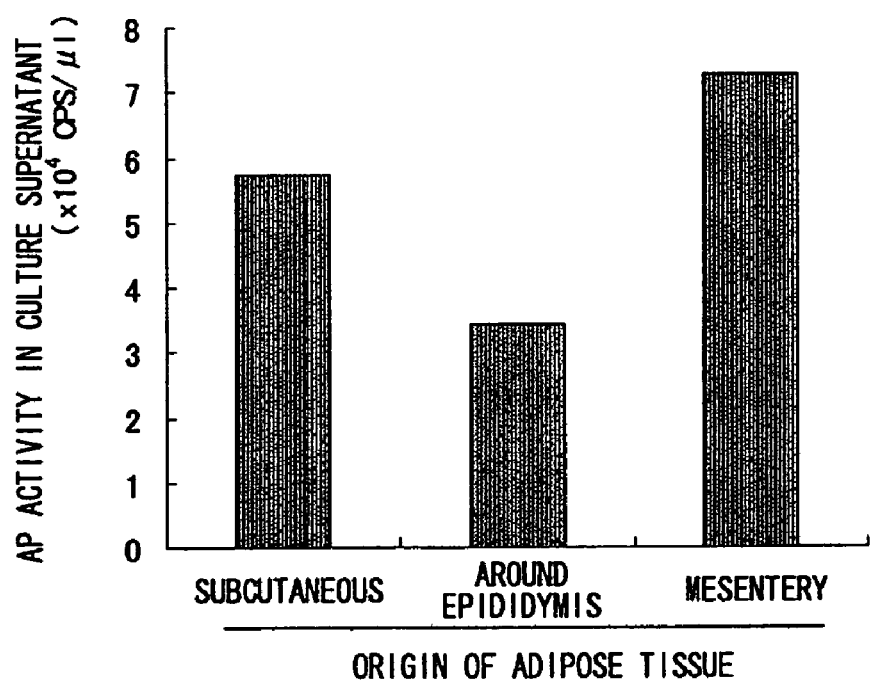
FIG. 3 shows a comparison of gene transfer efficiency when retroviral vector MLV(VSV)/pBabeCL(PLAP) IP is transduced to primary cultured adipocytes derived from various adipose tissues.

Adipocytes to be used for gene transfer (derived from subcutaneous fat, fat surrounding the epididymis, and mesenteric fat of ICR mice, and the subcutaneous fat of C57BL/6 mice) were prepared in 6-well or 96-well plates so that they were 50 to 80% confluent by the day before transfection. The medium was discarded, and equal amounts of 4 μg/mL Polybrene (SIGMA) solution and virus solution were added to the cells to transduct the viral vector. Eight hours after transduction, the medium was changed to a normal medium, and further culturing and subculturing were performed. The AP activity of a portion of the cells was measured by collecting the 24-hour culture supernatant on day four after transfection (FIG. 3).

Figure 5:
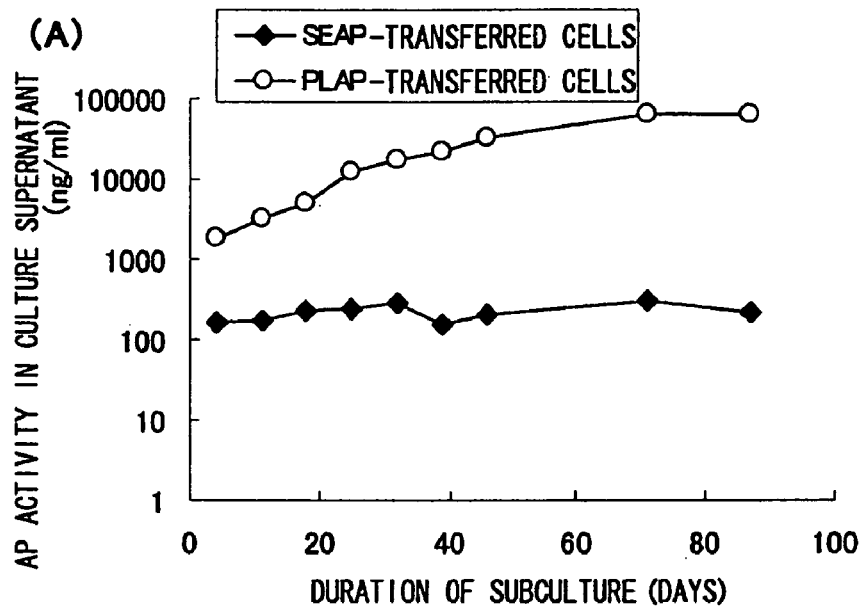
FIG. 5 shows the duration of AP expression in subcultures of primary cultured adipocytes transduced with an AP-expressing viral vector. (A) shows the result of transferring SEAP gene (MLV(VSV)/pBabeCL(SEAPmh)I2G) or PLAP gene (MLV(VSV)/pBabeCL(PLAP)IP) to cells derived from C57BL/6 mice subcutaneous fat. (B) shows the result of transferring PLAP gene (MLV(VSV)/pBabeCL(PLAP)IP) or GFP gene (MLV(VSV)/pBabeCL(GFP)IP) into adipocytes derived from ICR mice.
Figure 5:
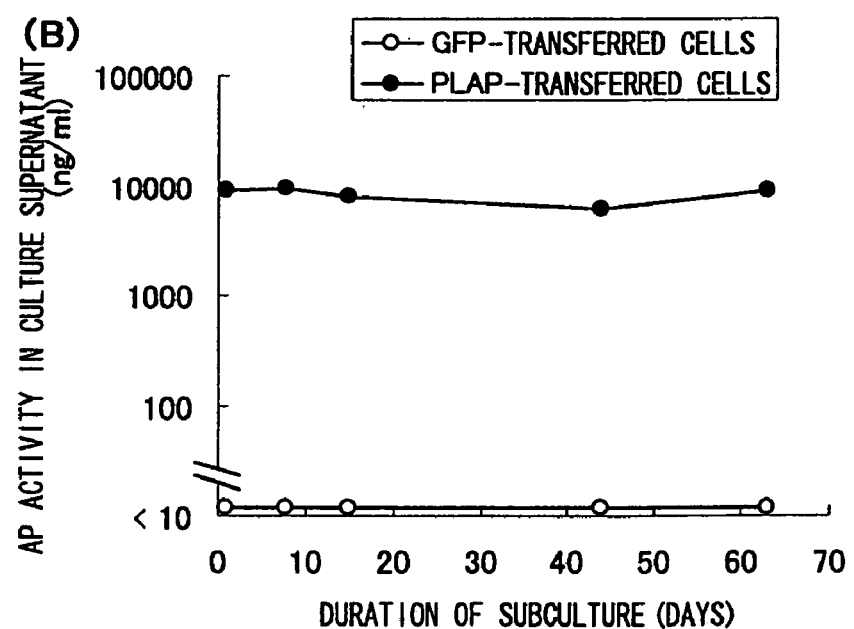
Figure 6:
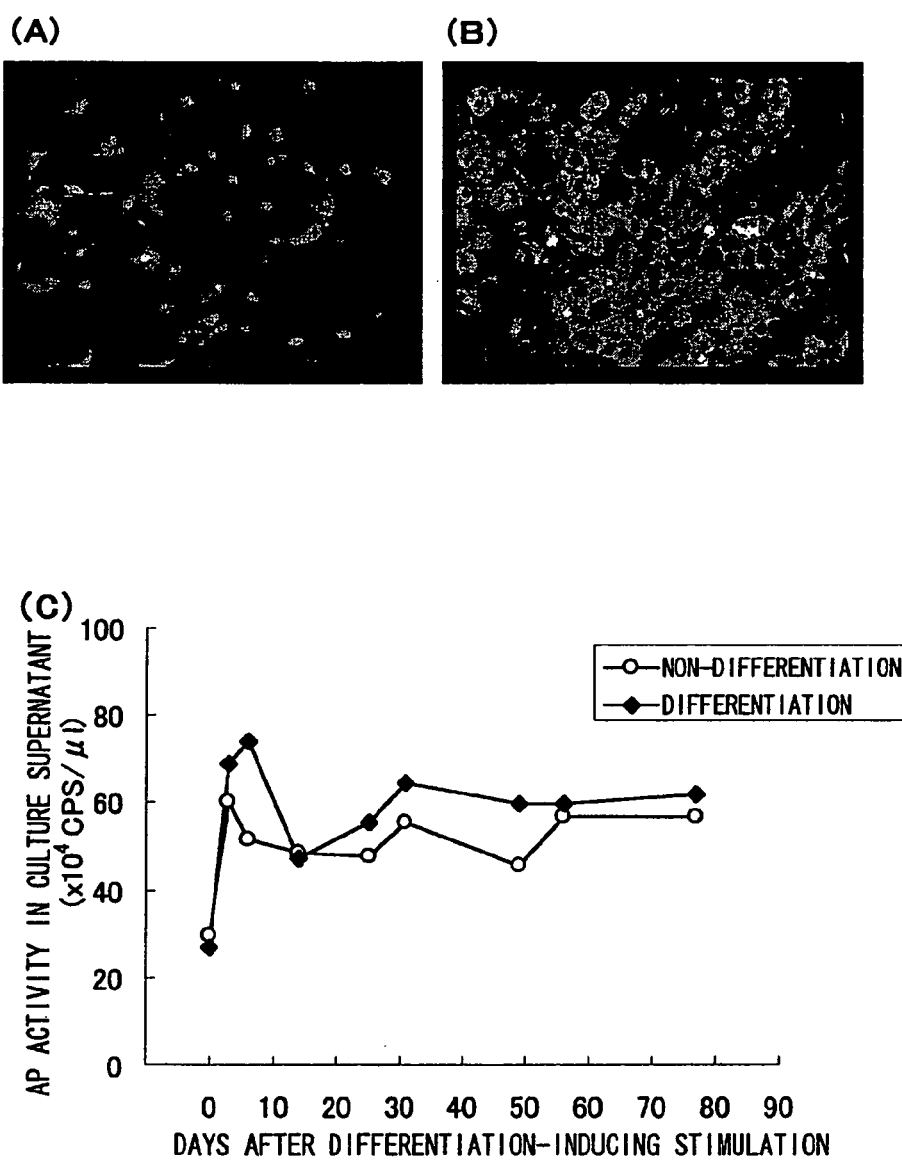
FIG. 6 is a set of photographs and a graph showing the change in expression in differentiation-induced gene-transferred adipocytes. (A) shows a GFP light microscope image of primary cultured adipocytes under non-differentiation-inducing conditions, where the adipocytes transfected with MLV(VSV)/pBabeCL(GFP)IP are derived from ICR subcutaneous fat. (B) shows a similar GFP microscope image taken under differentiation-inducing conditions. (C) shows AP production by MLV (VSV)/pBabeCL (PLAP) IP-transfected primary cultured adipocytes (derived from ICR subcutaneous fat) under non-differentiation-inducing conditions (non-differentiation) and differentiation-inducing conditions (differentiation).

Subculturing was performed according to the method of Example 1 on a 10-cm-dish scale. Cells were cultured for four to seven days, and medium was exchanged on reaching confluence. AP activity was measured in the culture supernatant 17 hours later. These cells were continuously subcultured and by appropriately performing similar manipulations, maintenance of expression was examined (FIGS. 5 and 6). AP activity was not measured every time subculturing was performed.

Figure 4:
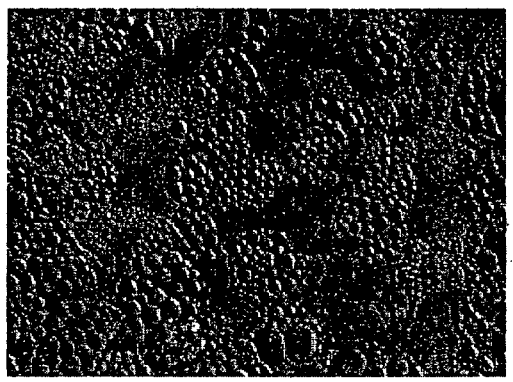
FIG. 4 is a set of microphotographs showing images of the differentiation induction of primary cultured adipocytes transduced with MLV(VSV)/pBabeCL(GFP)IP. (A) and (B) respectively show a light-microphotograph, and a GFP fluorescence photograph of the same visual field.
Figure 4:

Differentiation was induced in 6-well plates according to the method of Example 1. However, treatment was performed for three days with induction medium, which was replaced with maturation medium every three days thereafter. The AP activity of the culture supernatant was measured using the culture supernatant obtained every three days, and the x-axes in the figures show the day on which the supernatant was collected. For the GFP-transfected cells, microphotographs were taken under appropriate GFP light (FIGS. 4 and 6). Non-differentiation-inducing conditions refer to conditions in which culturing is continued in a normal medium instead of an induction medium or mature medium.

[Results]

FIG. 3 is a comparison of the gene transfer efficiency for each kind of tissue-derived cell when using retroviral vectors. AP activity was confirmed in the culture supernatant of all cells when gene transfer was performed on the primary cultured adipocytes isolated from each of the adipose tissues existing in the inguinal subcutaneous tissue, area around the epididymis, and mesentery of ICR mice. This showed that retroviral vectors can transfer genes regardless of the site of cell origin.

FIG. 4 is a set of microphotographs showing images of the differentiation induction of cells transducted with a GFP-expressing retroviral vector. Differentiation induction was initiated 13 days after gene transfer, and the photographs were taken three weeks later. GFP fluorescence was observed in cells containing lipid droplets, which showed that the viral vector can transfer genes into preadipocytes that possess the ability to differentiate, and that gene transfer by the vector does not affect their ability to differentiate.

FIG. 5 shows the continuity of expression in the subcultures of primary cultured adipocytes transfected with an AP-expressing viral vector. AP activity was measured in culture supernatant taken 17 hours after cells reached confluency in a 10-cm dish. Continuous AP production was confirmed over the 87 days for which primary cultured adipocytes derived from C57BL/6 mice subcutaneous fat were examined (A), and over the 63 days for which primary cultured adipocytes derived from ICR mice subcutaneous fat were examined (B). These results showed that transduction of the viral vector to primary cultured adipocytes can produce stable expression cells that maintain the foreign genes in the daughter cells produced after division.

FIG. 6 is a set of photographs and a graph showing changes of expression in differentiation-induced gene-transferred adipocytes. GFP-expressing adipocytes derived from ICR subcutaneous fat showed strong GFP expression under both normal culture conditions (A), and differentiation-inducing conditions (B). Furthermore, AP-expressing adipocytes derived from ICR subcutaneous fat showed continuous expression of AP under both non-differentiation-inducing conditions (non-differentiation) and differentiation-inducing conditions (differentiation) (C). The primary cultured adipocytes that were gene transferred by the viral vectors were found to stably express genes at any phase, not only under the proliferation conditions described in FIG. 5, but also under non-differentiation-inducing conditions, or more specifically under non-proliferative conditions or mature conditions.

EXAMPLE 4

Production, by Using a Plasmid Vector, of Adipocytes that Stably Express Insulin Methods of gene transfer include methods that use plasmid vectors.

[Methods]

(1) Isolation and Modification of the Human Insulin Gene

PCR was performed on a human pancreas-derived cDNA library (Stratagene), using the primers shown in Table 1 (Insulin Fw and Rv). A human insulin gene fragment was obtained. The nucleotide sequence of this obtained 354-bp fragment was determined, and the fragment was subcloned into pCR2.1TOPO vector (Invitrogen) as native insulin.

modified form (s1s2B10), or an empty vector (mock), was transfected into adipocytes derived from the adipose tissue

TABLE 1

Primer sequences used for PCR

| Primer | Nucleotide sequence (5'-) | |
|---|---|---|
| Insulin Fw | CATAAGCTTACCATGGCCCTGTGGATGCGC | (SEQ ID NO: 1) |
| Insulin Rv | CATTCTAGACTAGTTGCAGTAGTTCTCCAG | (SEQ ID NO: 2) |
| site1 | CTTCTACACACCCAGGACCAAGCGGGAGGCAGAGGAC | (SEQ ID NO: 3) |
| site2 | CCCTGGAGGGATCCCGGCAGAAGCGTGG | (SEQ ID NO: 4) |
| B10 | CACCTGTGCGGATCCGACCTGGTGGAAGC | (SEQ ID NO: 5) |
| sPL-GLP-1Fw | TTCCACCATGCTGCTGCTGCTGCTGCTGCTGGGCCTGAGGCTACAGCTCT-CCCTGGGCCATGCTGAAGGGACCTTTACCAGTG | (SEQ ID NO: 6) |
| sPL-GLP-1Rv | AATTATCCTCGGCCTTTCACCAGCCAAGCAATGAACTCCTTGGCAGCTTG-GCCTTCCAAATAAGAACTTACATCACTGGTAAAGGTCCCTTCAGC | (SEQ ID NO: 7) |
| GLP-5' | TTCCACCATGCTGCTGCTGC | (SEQ ID NO: 8) |
| GLP-3' | AATTATCCTCGGCCTTTCACCAG | (SEQ ID NO: 9) |

(The bold letters denote the initiation codon in Fw, and the antisense of the stop codon in Rv. The underline indicates mutated portions.)

Next, in order to express mature insulin in the adipocytes, genetic modification was performed based on literature (JBC, 1994, 269(8), 6241-). More specifically, primers of both directions were individually synthesized to contain mutations at each of the junction sites between the human insulin B chain and the C peptide (site1), between the same C peptide and A chain (site2), and the 10th histidine residue of the B chain (B10) (Table 1). The mutants were obtained using a Quikchange mutagenesis kit (Stratagene). Performing this reaction on site1 and site2 yielded the s1s2 mutant. Performing the reaction on site1, site2, and B10 yielded s1s2B10 mutant insulin. After confirming the nucleotide sequence of the obtained modified human insulin gene, the gene was incorporated into pcDNA3.1 vector, and then used for gene transfer.

(2) Gene Transfer into Primary Cultured Adipocytes

After mixing 500 μL of FCS-free DMEM medium and 15 μL of Fugene 6 reagent (Roche), 5 μg of transfection plasmid was added, and then this was left to stand at room temperature for 15 minutes. The mixed solution was added to primary cultured adipocytes (derived from adipose tissue around the C57BL/6 mice epididymis), which had been cultured to 70 to 80% confluency in a 10-cm dish. This was cultured for 24 hours in a $CO_2$ incubator. Four days after gene transfer, the cells were subcultured in a T225 flask, and cultured overnight. The medium was then exchanged for a medium comprising 0.2 mgU/mL of G418 (SIGMA), and culture was continued for three weeks, whereupon gene-transferred cells were selected. The obtained G418-resistant cells were plated onto a 10-cm dish, and the amount of insulin in the culture supernatant was measured using an ultrasensitive insulin EIA kit (Morinaga). This EIA kit detects both proinsulin, which has not yet been processed, and mature insulin.

[Results]

Figure 7:
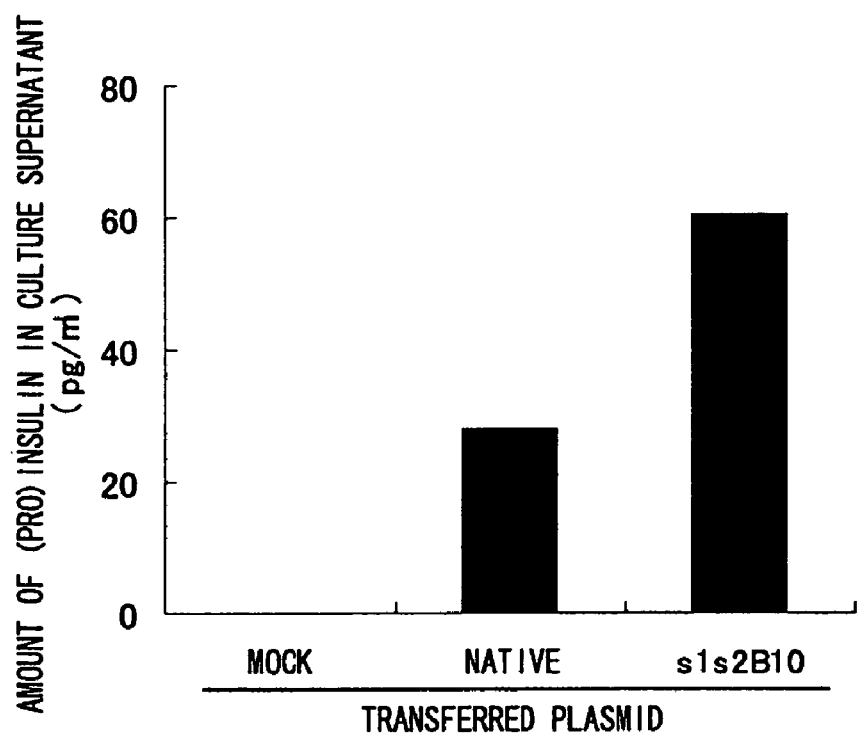
FIG. 7 shows (pro)insulin production by plasmid transfection into primary cultured adipocytes.

FIG. 7 shows (pro)insulin production by plasmid transfection into primary cultured adipocytes. Each of pcDNA3.1Myc-His vectors individually incorporating the native human insulin gene (native) and the site1/site2/B10- modified form (s1s2B10), or an empty vector (mock), was transfected into adipocytes derived from the adipose tissue surrounding the C57BL/6 mice epididymis. Human (pro) insulin was detected in the culture supernatant of resistant cells obtained by G418 selection. This showed that stable gene transfer to primary cultured adipocytes is also possible using a plasmid vector.

EXAMPLE 5

Production, Using an Adeno-associated Virus, of Adipocytes that Stably Express AP Methods of gene transfer include methods that use adeno-associated viruses (AAV).

[Methods]

The study was carried out using AAV Helper-Free System (Stratagene). The PLAP fragment of Example 2 (a fragment excised by using HindIII and BglII) was inserted into the same restriction enzyme site of the pAAV-MCS vector, yielding pAAV-PLAP.

AAV vector production was carried out as follows: 1.75 mL of OPTI-MEM (Invitrogen) was mixed with 220 μL of the plasmid transfection reagent Fugene, then 25 μg each of PAAV-PLAP, pAAV-RC, and pHelper were mixed in, and these were left to stand at room temperature for 15 minutes (Fugene/plasmid solutions). Meanwhile, 293-EBNA cells grown to 60 to 70% confluency in a 15-cm dish were prepared. The culture solution was changed to FCS-free DMEM, then Fugene/plasmid solution was instilled evenly, and this was cultured for two to three hours. FCS was then added to a final concentration of 10%, and this was cultured for two more days. The cells were collected by trypsin treatment and centrifugation, and then suspended in 50 mM Tris-HCl and 150 mM NaCl solution so that the final volume was 3 mL. Cells were disrupted by performing three cycles of dry ice-ethanol/37° C. freeze-thawing on this suspension solution. Furthermore, after degrading the host genomic DNA using Benzonase (SIGMA), the virus solution was produced by centrifugation at 9,000 rpm for 30 minutes, followed by filtration of the supernatant.

Primary cultured adipocytes (derived from C57BL/6 mice subcutaneous fat) were plated onto a 12-well plate at $1 \times 10^4$ cells/well the day before gene transfer, and were cultured. They were then treated for six hours in a medium containing 40 mM of Hydroxyurea and 1 mM of butyric acid (both from SIGMA). After removing this medium, 0.5 mL/well of the virus solution, diluted to 1/100 with FCS-free DMEM, was added. After culturing for one hour, FCS-containing medium was added to a final concentration of 10%, and this was cultured overnight. Thereafter, normal medium exchanges were performed, and subculturing was performed on the 24th day.

Medium was exchanged on the first, seventh, and 25th day of transfer, and the culture supernatant collected two days after each exchange were used for the AP assays. 10 μL of the supernatant, which was diluted as necessary, was warmed at 65° C. for 20 minutes, then 50 μL of assay buffer (16 mM $NaHCO_3$, 12 mM $Na_2CO_3$, 0.8 mM $MgSO_4$), and 50 μL of luminescent stain reagent (CDP-Star Ready to Use with Sapphire II, TROPIX), were mixed, reacted in the dark for 30 minutes, and then measured with a luminometer.

[Results]

Figure 8:
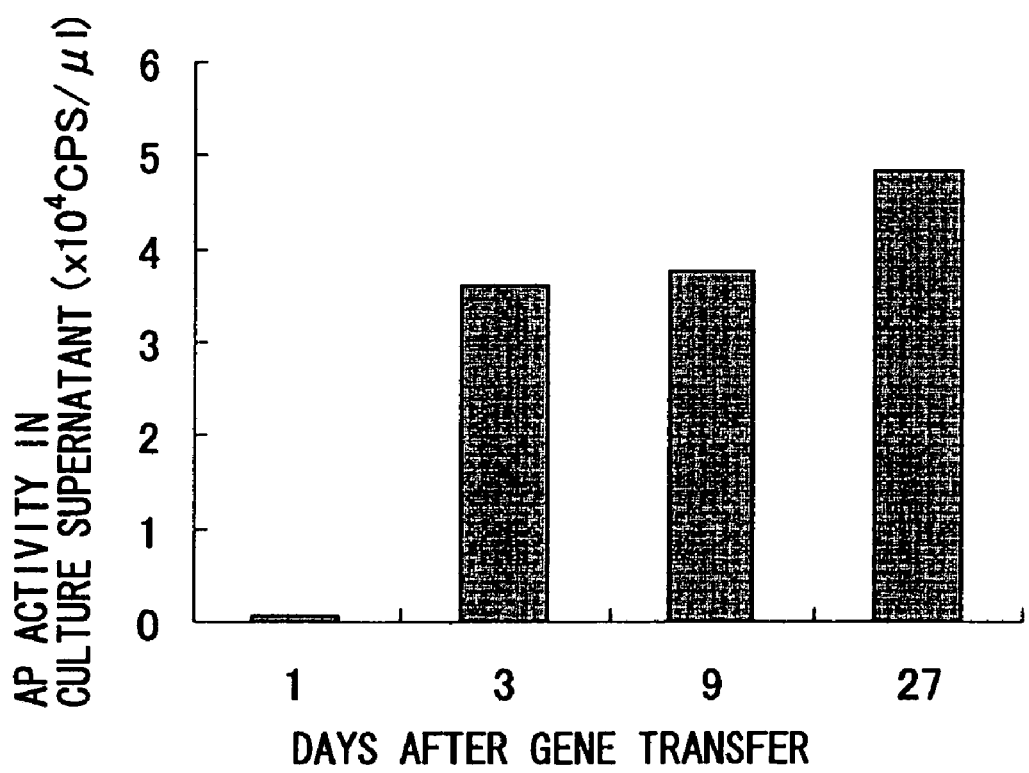
FIG. 8 shows the stable expression of AP in primary cultured adipocytes (derived from C57BL/6 mice subcutaneous fat) transfected with AP-expressing AAV.

FIG. 8 shows stable expression of AP in primary cultured adipocytes (derived from C57BL/6 mice subcutaneous fat) transfected with AP-expressing AAV. AP activity was detected in the culture supernatant over the entire examination period. This showed that stable gene transfer to primary cultured adipocytes can be accomplished using an AAV vector.

EXAMPLE 6

Construction of a Human Insulin-expressing Retroviral Vector, and Transduction Thereof into Adipocytes

[Methods]

The modified human insulin gene constructed in Example 4 (s1s2B10Ins) was inserted into pBabeCLXI2G vector following the method of Example 3 (pBabeCL(s1s2B10Ins)I2G). This plasmid along with a VSV-G-encoding vector (pVPack-VSV-G/Stratagene), and Gag-Pol-encoding vector (modified from pVPack-gp/Stratagene) were introduced into 293-EBNA cells according to the method of Example 3, thus producing the modified insulin-expressing retroviral vector (MLV(VSV)/pBabeCL(s1s2B10Ins)I2G). The culture supernatant (approximately 200 mL) of 293-EBNA cells from twenty-two 10-cm dishes was collected, insoluble material was removed by centrifugation/filtration treatment, and then the concentrated virus solution was yielded by ultracentrifugation (19,500 rpm, 100 minutes) This was transferred to primary cultured adipocytes (derived from C57BL/6 subcutaneous fat), which had been plated onto a 6-well plate on the previous day.

The gene-transferred cells were re-plated onto a 6-well plate, and differentiation was induced according to the method of Example 1. Culture supernatants were each collected for three days, from three days before induction to the day of induction initiation (pre-induction), and for three days from the 14th to 17th day of induction (post-induction). The amount of insulin was assayed by the same method as in Example 4. Furthermore, to confirm that processing occurred at the desired sites, and that mature insulin was produced, measurements were made using insulin EIA kit (IBL), which only recognizes mature insulin. The culture supernatant of non-gene-transferred cells, which were simultaneously subjected to differentiation induction, was used as a control.

[Results]

Figure 9:
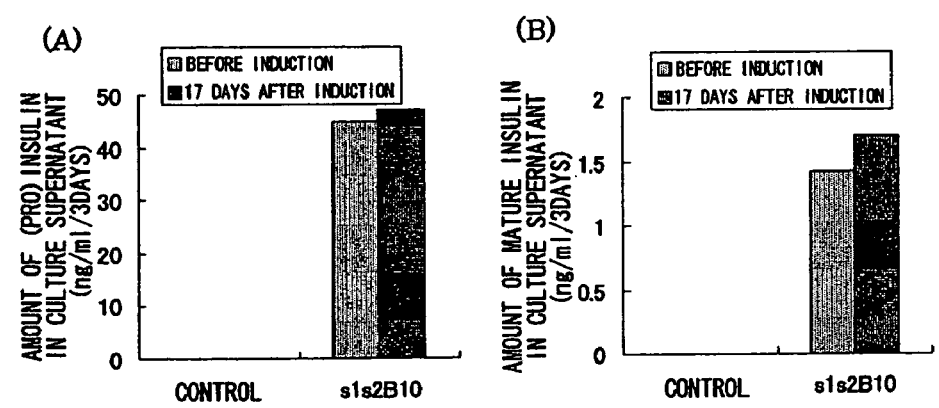
FIG. 9 shows insulin expression at the time of differentiation induction in primary cultured adipocytes transfected with s1s2B10 insulin-expressing retroviral vector. (A) shows the results using an EIA produced by Morinaga and (B) shows the results using an EIA produced by IBL.

FIG. 9 shows insulin expression at the time of differentiation induction in primary cultured adipocytes transducted with s1s2B10 insulin-expressing retroviral vector. (A) shows the results of using EIA produced by Morinaga, and (B) shows the results of using EIA produced by IBL. These results show that insulin is stably secreted both before and after differentiation induction, and that transfer of mutant insulin gene may cause the production of mature insulin from adipocytes.

EXAMPLE 7

Construction of a Retroviral Vector that Expresses Human Glucagon-like Peptide-1 (GLP-1), and Transduction Thereof into Adipocytes GLP-1 is a peptide that is produced from small intestinal L-cells during food intake, and comprises the effect of stimulating insulin secretion by acting on pancreatic β-cells. GLP-1 is also known to have a variety of other antidiabetic and antiobesity effects such as a regeneration effect on pancreatic β-cells, an appetite-suppressing effect, and an inhibitory effect on gastric emptying (Meier, J. J. et al. Eur. J. Pharmacol. 2002, 12; 440(2-3):269-79; Drucker, D. J. Gastroenterology 2002; 122(2): 531-544). A peptide comprising positions 7 to 37 of the amino acid sequence of GLP-1 (or up to position 36 in the amide form), is formed by tissue-specific processing of the polypeptide produced from the preproglucagon gene, and is known to comprise the main pharmacological activity (Drucker, D. J. et al. Proc. Natl. Acad. Sci. USA. 1987 May; 84(10):3434-3438; Kreymann, B. et al. Lancet. 1987, 5; 2(8571):1300-1304; Mojsov, S. et al. J. Clin. Invest. 1987 Feb; 79(2): 616-619). The following examination was carried out in order to produce this factor from adipocytes.

[Methods]

A nucleotide sequence with a total of 156 base pairs was designed, comprising a sequence (SEQ ID NO: 10 shows the coding sequence; SEQ ID NO: 11 shows the amino acid sequence) in which human GLP-1 (7-37) and a stop codon are linked to the signal peptide (17 amino acids) of the PLAP gene used in Example 3. Nucleotides were synthesized so that a 22mer overlap was comprised at the center (sPL-GLP-1Fw and sPL-GLP-1Rv in Table 1). These were annealed and a double strand was formed using Pfu polymerase (Stratagene). The target fragment was then amplified by PCR using 5'-end and 3'-end primers (GLP-5' and GLP-3' in Table 1). This fragment was subcloned into pCR2.1 vector, then excised using restriction enzymes, and subsequently inserted into pBabeCLXI2G vector, as in Example 3 (pBabeCL(sPL-GLP1)I2G). This was transfected into 293-EBNA cells by a method similar to that of Example 6, producing a GLP-1-expressing retroviral vector (MLV(VSV)/pBabeCL(sPL-GLP-1)I2G). Approximately 90 mL of the culture supernatant of 293-EBNA cells from nine 10-cm dishes was collected. Insoluble material was removed by centrifugation/filtration treatment, and the supernatant was then ultracentrifuged (19,500 rpm, 100 minutes) to yield a concentrated virus solution. This was transducted into primary cultured adipocytes (derived from C57BL/6 subcutaneous fat) that had been plated onto a 6-well plate the previous day. The transfected adipocytes were again plated onto a 12-well plate, and differentiation induction was carried out according to the method of Example 1. "Non-induced" refers to a condition in which culture was continued in a normal medium instead of in an induction medium or mature medium. Seven days later, the medium was exchanged to FCS-free DMEM medium comprising 1 mM Valine-pyrrolidine (GLP-1 degradation enzyme inhibitor; synthesized at Eisai). The culture supernatant was collected 18 hours later, and the amount of active GLP-1(7-37) was measured using ELISA (LINCO).

[Results]

Figure 10:
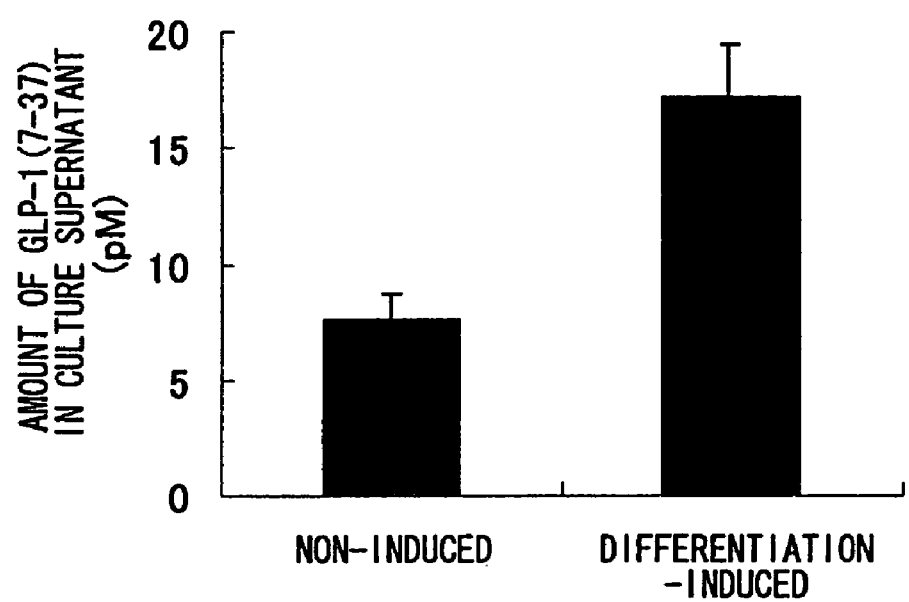
FIG. 10 shows the expression of GLP-1 (7-37) in primary cultured adipocytes transfected with GLP-1(7-37)-expressing retroviral vector. Measurements were made in triplicate, and their average values and standard deviations are shown.

FIG. 10 shows the level of expression in primary cultured adipocytes transfected with GLP-1(7-37)-expressing retroviral vector. Expression of active form GLP-1(7-37) was observed in the culture supernatant of both non-differentiation-induced and differentiation-induced adipocytes. This showed that even when a factor is produced as the prepro-type and then cut out by processing, this method allows production of only that factor from adipocytes.

EXAMPLE 8

Implanting Mice with Cells that Stably Express AP (Test 1)

[Methods]

After culturing the AP-expressing adipocytes (transducted with MLV(VSV)/pBabeCL(PLAP)IP; derived from C57BL/6 subcutaneous fat) produced by the method of Example 3 to confluency, the cells were collected by trypsin treatment, washed with PBS, and suspended at $5 \times 10^6$ cells/mL in ice-cold Matrigel (Becton Dickinson). Implantation was performed by injecting this to the dorsal subcutaneous area (Sc) of C57BL/6 mice (eight weeks old at the time of operation; Charles River) at a dose of 0.2 mL per mouse ($1 \times 10^6$ cells/head) (without differentiation induction). On the other hand, the same cells were cultured to confluency, then cultured for three days in the inducing medium of Example 1, and then implanted by similar methods (with differentiation induction). Blood was collected over time by the method indicated in Example 2, and AP activity in the plasma was measured.

[Results]

Figure 11:
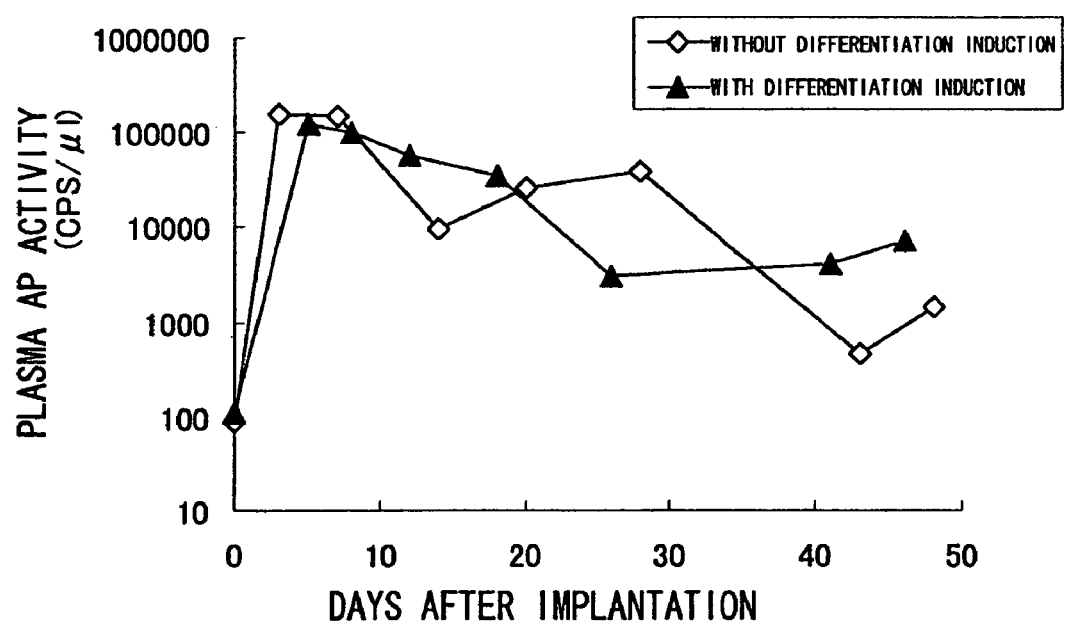
FIG. 11 shows the effect of the presence or absence of pre-implantation stimulation of differentiation induction on in vivo AP expression in the implantation of AP-expressing primary cultured adipocytes.

FIG. 11 shows the change in plasma AP activity in mice implanted with AP-expressing primary cultured adipocytes. Individuals that received an implant of cells subjected to differentiation-inducing stimulation for three days before implantation ("with differentiation induction") showed less fluctuation in the continued expression than individuals that received an implant of cells that were not induced. However, both methods of implantation showed continued expression over the entire 50 or so days of examination. This shows that the post-transplantation survival rate of cells may be improved by providing differentiation-inducing stimulation.

EXAMPLE 9

Implanting Mice with Cells that Stably Express AP (Test 2)

[Methods]

(1) Implantation

The AP-expressing adipocytes (transducted with MLV (VSV)/pBabeCL(PLAP)IP; derived from ICR subcutaneous fat) produced in Example 3 were cultured to confluency. The cells were collected by trypsin treatment, washed with PBS, and suspended at $5 \times 10^6$ cells/mL in an ice-cold Matrigel (Becton Dickinson) to which 1 µg/ml of bFGF (Genzyme Techne) was added. Implantation was performed by injecting this at a dose 0.2 mL per mouse ($1 \times 10^6$ cells/head) to each site (dorsal subcutaneous area (Sc), inguinal subcutaneous fat (fat), and intraperitoneal region (ip)), of the ICR nude mice (six weeks old at the time of operation, Charles River). As a control, GFP-expressing adipocytes were treated similarly and implanted into the subcutaneous tissue.

Some of the AP-expressing cells were cultured for three days by the induction medium of Example 1, and then collected and implanted in the same manner (Dif). After using the induction medium, some of these cells were cultured for four days in a maturation medium, and then collected and implanted in the same manner (Mat).

Furthermore, some of the AP-expressing cells were plated onto an 8-well-Labteck chamber (Nunc) under the same conditions used for implantation ($1 \times 10^6/0.2$ mL bFGF-added Matrigel), and the cells were solidified by heating at 37° C. Implantation was accomplished by inserting this solidified gel into the mouse subcutaneous area. Herein, cells cultured in a normal medium after solidification were referred to as pre-fixed (pf)/gr, and cells cultured in a differentiation-inducing medium were referred to as pf/dif. Implantation was carried out after seven days of culturing.

AP activity in the plasma was measured over time, before implantation (day 0) and after implantation, according to the method of Example 2.

(2) Extirpation

In the group implanted after differentiation induction (Dif/Sc), the implanted cell masses were extirpated, along with the Matrigel, from individuals A and B, five and 43 weeks after implantation, respectively. Extirpation was performed on the control sample in the fifth week since implantation. Each individual was intraperitoneally administered with 50 mg/kg of Nembutal, as anesthesia. Their skin was then incised and a visually confirmed implanted Matrigel section was extirpated. The site of the surgery was sutured and disinfected with Isodine (Meiji). The animals were then raised in the same manner, and blood was collected over time.

[Results]

Figure 12:
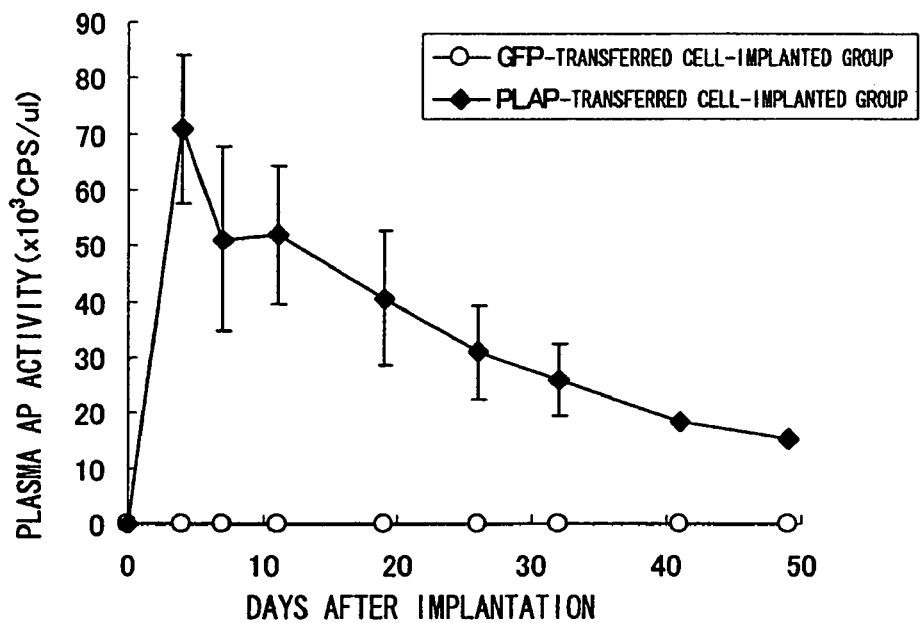
FIG. 12 is a set of graphs and a photograph. (A) shows the change in plasma AP activity when AP-expressing primary cultured adipocytes are implanted in the presence of differentiation stimulation using a basic FGF-supplemented Matrigel. (B) shows the loss of plasma AP activity on extirpation of the implanted Matrigel (individual A). (C) shows a GFP light microscope image of the Matrigel extirpated from the control group which received GFP-transfected cells. For the PLAP-implanted group shown in (A), the values shown are the group average and standard deviation of values measured for each individual up to the 32nd day. The remaining values are average values.
Figure 12:
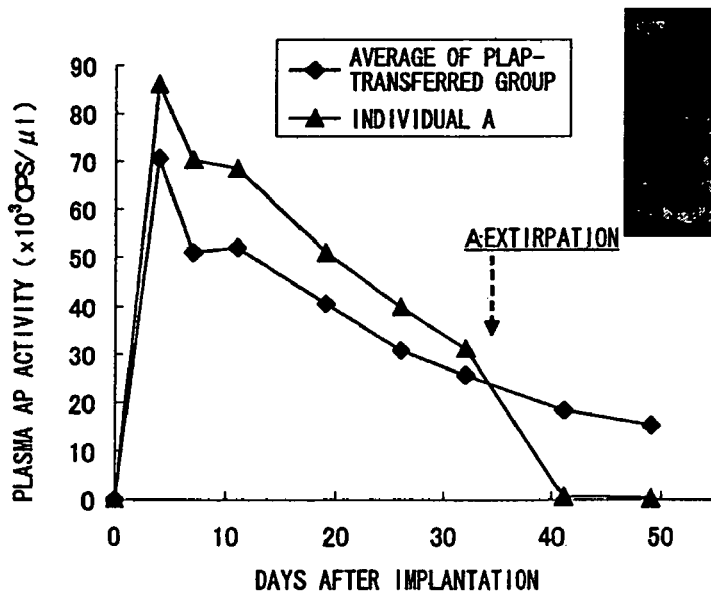
Figure 12:

FIG. 12 (A) shows the result of examining the change in plasma AP activity over 50 days, when AP-expressing primary cultured adipocytes were implanted using basic FGF-added Matrigel, in the presence of differentiation stimulation (Dif/Sc group). Change in blood AP activity was stable for 49 days over an about 5-fold range. This showed that bFGF addition at the time of implantation can further improve the post-implantation engraftment rate. (B) shows the disappearance of plasma AP activity due to the extirpation of the implanted Matrigel (individual A) over the same period. AP activity in the extirpated individuals was significantly decreased compared to the average value for the PLAP transducted group. This showed that blood AP is derived from the implanted cells, and that graft extirpation can quickly eliminate gene expression. At this time, extirpation was also performed on a portion of the control group, which was implanted with GFP-transfected cells. GFP-positive cells were found in the extirpated Matrigel, and many of them displayed a vacuole image (C) similar to that shown in FIG. 6(B). This showed that primary cultured adipocytes implanted by this method may be engrafted as mature adipose tissue in vivo.

Figure 13:
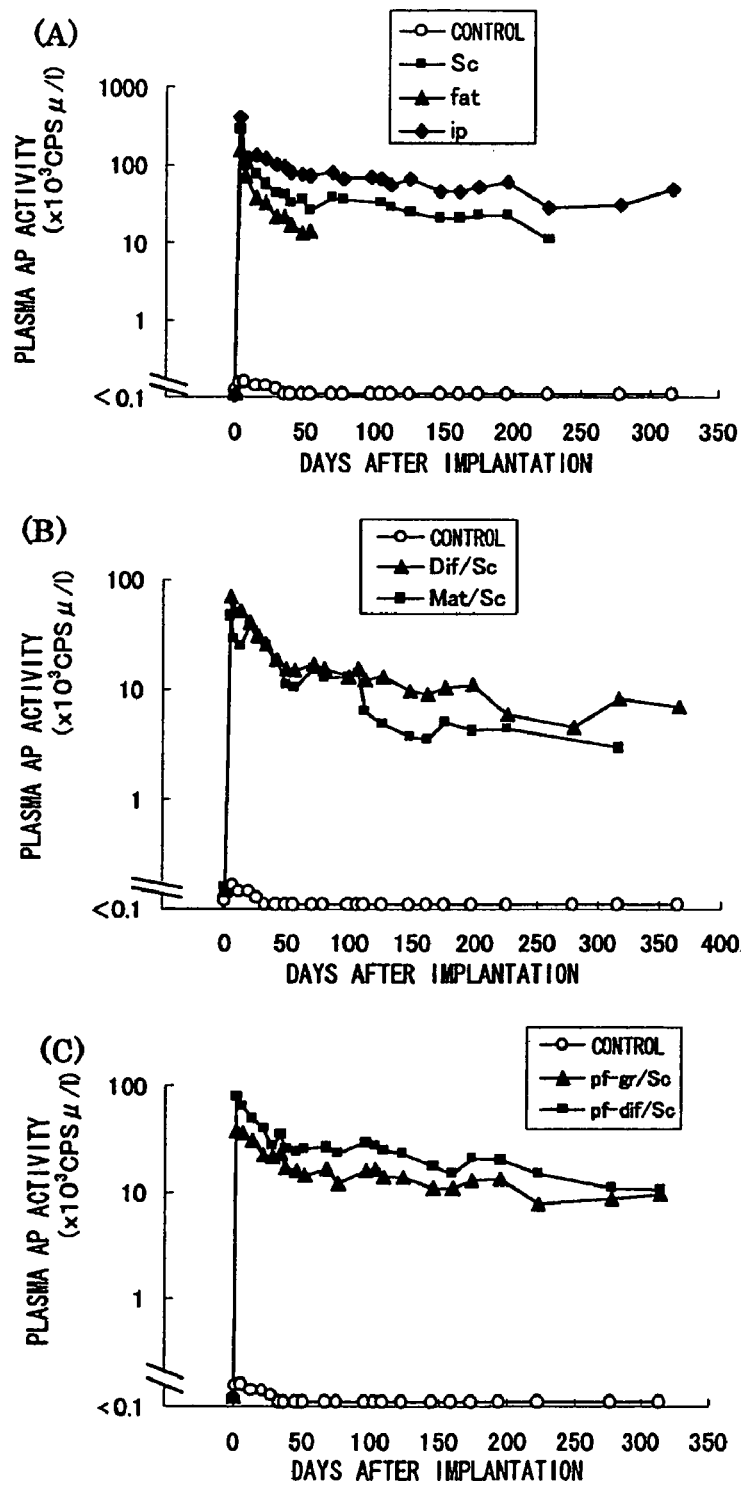
FIG. 13 shows the results of the long-term examination of AP activity in the blood of mice receiving an implant by the method of FIG. 12(A), and by a variety of other methods.

FIG. 13 shows the result of a long-term examination of blood AP activity in the implanted mice of FIG. 12(A), and in mice receiving an implant by a variety of other methods. In the group implanted with PLAP-transfected cells, a clear increase of blood AP activity was confirmed for all implantation sites and implantation methods. Blood AP activity was maintained for a long period, and in particular, stable AP expression was observed for one year during the Dif/Sc group testing period (the group described in FIG. 12(A)). Continuous AP production was also confirmed for the other implantation methods, all during the examination period (316 days for the ip group, 54 days for the fat group, 225 days for the Sc group, 317 days for the Mat/Sc group, and 314 days for the two pre-fix groups). The peak of activity observed within one week of implantation was highest in the ip group. The highest values were then in the order of Sc>fat>Dif/Sc≅pf–dif>pf–gr≅Mat/Sc. The range of variation after implantation was observed as a ratio between the activity after 13 weeks and the peak activity, which can be compared in all groups. Variance was smallest, approximately three-fold, in the two pre-fix groups, approximately five-fold in the ip, Dif/Sc, and Mat/Sc groups, and approximately ten-fold in the Sc and fat groups. The peak value immediately after implantation, and the range of variation after implantation differed for each implantation method. Any of these methods can thus be used according to the characteristics of the gene product used, the pathologic characteristics, and the simplicity of the technique. This showed that implantation of primary cultured adipocytes, to which genes were stably introduced ex vivo, can be performed by a variety of methods, and that long-term stable in vivo gene expression is possible after implantation.

Figure 14:
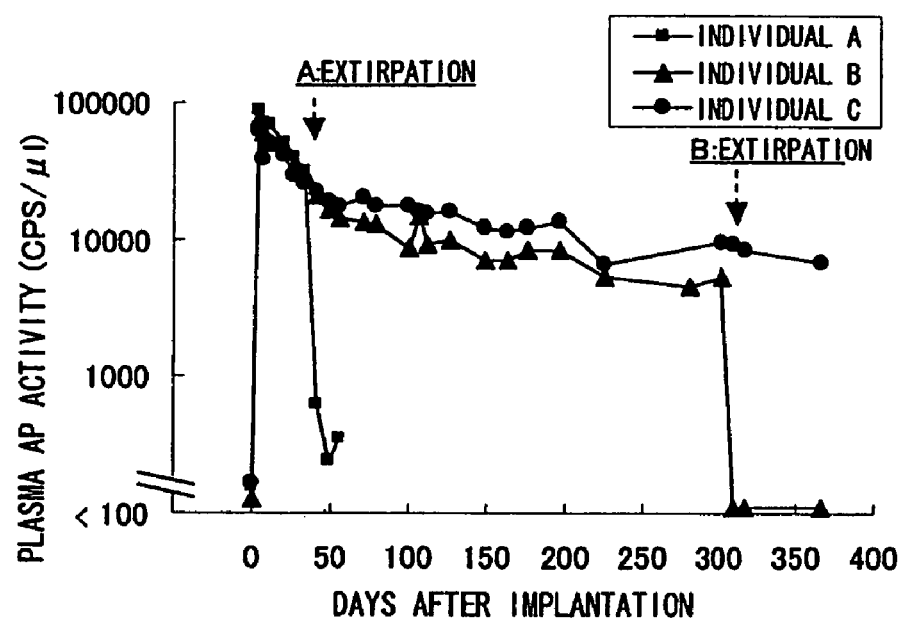
FIG. 14 shows the results of performing an extirpation test similar to that of FIG. 12(B) in the late stage of transplantation.

FIG. 14 shows the result of performing an extirpation experiment, similar to that described in FIG. 12(B), in the later stage of implantation. Blood AP activity after extirpation was confirmed to quickly disappear, not only in individuals in which extirpation was performed in the early stages of implantation (individual A), but also in individuals in which extirpation was performed in the later stages of implantation (individual B). This showed that adipocytes implanted by this method are localized at the implanted site for a long period after implantation, and their extirpation, when appropriate, can eliminate the gene expression regardless of the timing.

EXAMPLE 10

Transplanting Mice with Cells that Stably Express AP (Test 3)

The following examinations were carried out to confirm 'dose' dependence on the number of implanted cells

[Methods]

The AP-expressing adipocytes produced in Example 3 (transfected with MLV(VSV)/pBabeCL(PLAP)IP; derived from ICR subcutaneous fat) were cultured to confluency. The cells were cultured for three days in the induction medium indicated in Example 1, and then collected by trypsin treatment. After washing with PBS, the cells were suspended at $5 \times 10^6$ cells/mL into Matrigel. A five-fold stepwise dilution was carried out on the AP cell suspension solution using Matrigel, and $1 \times 10^6$ cells/mL and $2 \times 10^5$ cells/mL solutions were respectively prepared. bFGF was added to these solutions at a final concentration of 1 μg/mL, and they were then implanted to the dorsal subcutaneous area of ICR nude mice at a dose of 0.2 mL per mouse (high dose: $1 \times 10^6$ cells/head; medium dose: $2 \times 10^5$ cells/head; low dose: $4 \times 10^4$ cells/head). As a control, GFP-expressing adipocytes were similarly treated, and were implanted into the subcutaneous tissue under the same conditions as for high-dose conditions ($1 \times 10^6$ cells/head).

[Results]

Figure 15:
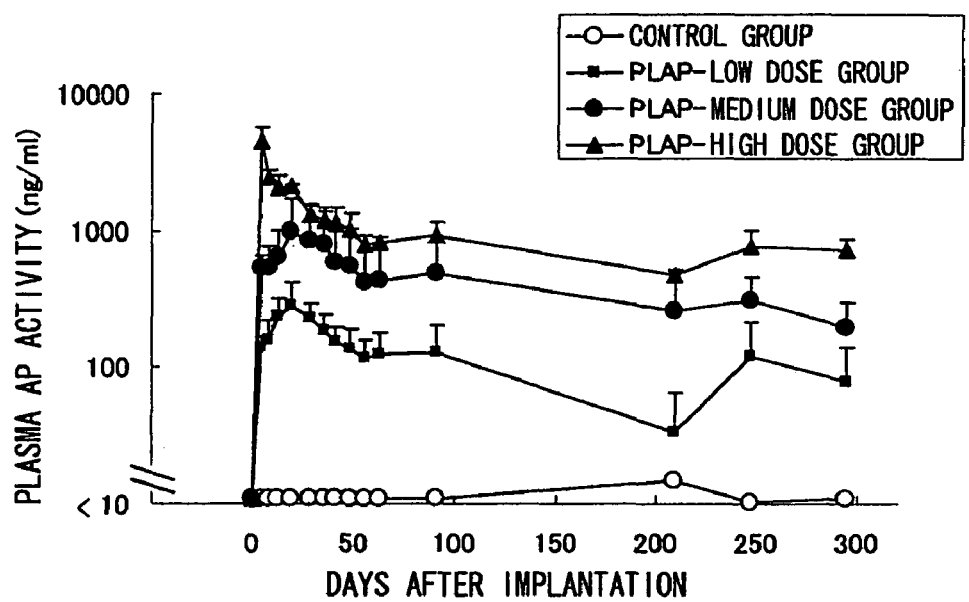
FIG. 15 shows the dependence of blood AP activity on the number of implanted cells when implanting AP-expressing adipocytes. The values indicated are the group average and standard deviation of the measurements of each individual.

FIG. 15 shows the dependence of blood AP activity on the number of implanted cells when implanting AP-expressing adipocytes. Dose-dependent blood AP activity was observed on changing the number of implanted cells, and this was not influenced by duration. More specifically, the medium or low dose groups did not show a peak at the early stage of implantation, which was observed in the high dose group, and the range of fluctuation was narrower. This showed that in vivo expression level can be easily adjusted using the number of implanted cells, and that by adjusting the optimal number of cells, the post-implantation blood concentration (expression level) can be stabilized.

EXAMPLE 11

Hypoglycemic Effect on Diabetes Model Mice due to Implantation of Insulin-Expressing Adipocytes

[Methods]

Diabetic mice were produced by intravenously administering eight-week old male C57BL/6 mice with 10 mL/kg of 170 mg/kg streptozotocin (STZ, SIGMA). Fasting blood glucose (FBG) levels were measured individually at one and two weeks after STZ administration, and individuals with an FBG of 300 mg/dl or more were determined to have diabetes. The blood sugar level was measured by performing a perchlorate treatment immediately after collection of whole blood, and then using Glucose Test-II (WAKO).

The MLV(VSV)/pBabeCL(s1s2B10Ins)I2G-transfected adipocytes produced in Example 6 were subjected to differentiation induction stimulation using the same method as in Example 10, and then suspended at $5 \times 10^6$ cells/mL in Matrigel to which 1 μg/mL of bFGF had been added. This suspension solution was implanted in the dorsal subcutaneous area of each diabetic mouse, at 0.2 mL per site, to a total of four sites (four×$10^6$/head). For the control group, non-gene-transferred adipocytes were implanted by the same method. Implantation was performed 19 days after STZ treatment, and thereafter, FBG level was measured over time. Statistical analysis was carried out by comparison with the control group (unpaired t test).

[Results]

Figure 16:
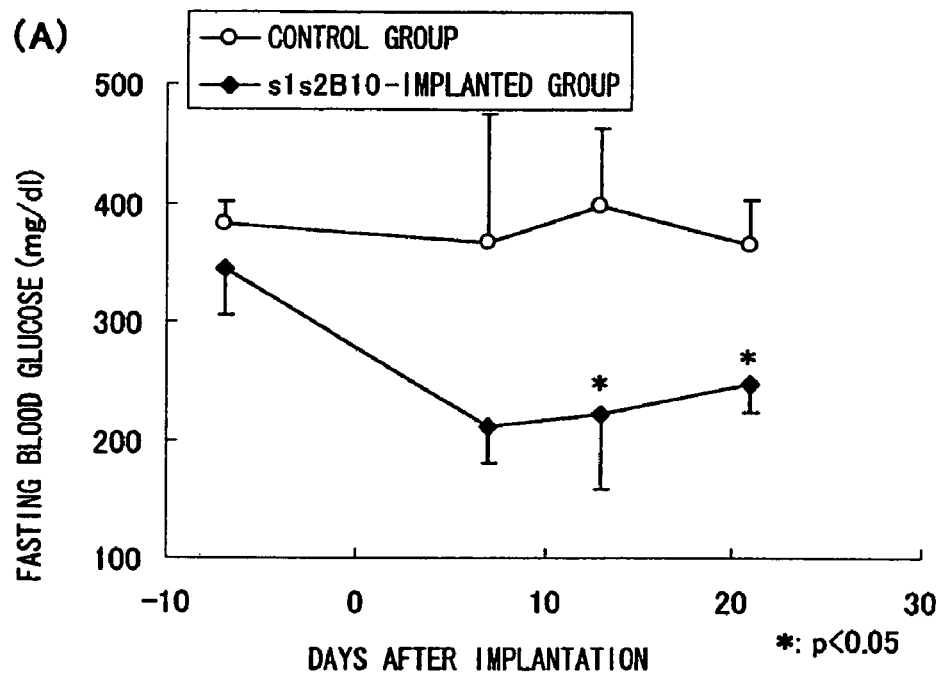
FIG. 16 shows the effect of implanting s1s2B10 insulin-expressing adipocytes to STZ-induced diabetic mice. (A) shows the effect on fasting plasma glucose level, and (B) shows the effect on body weight. The values indicated are the group average and standard deviation of the measurements of each individual.
Figure 16:
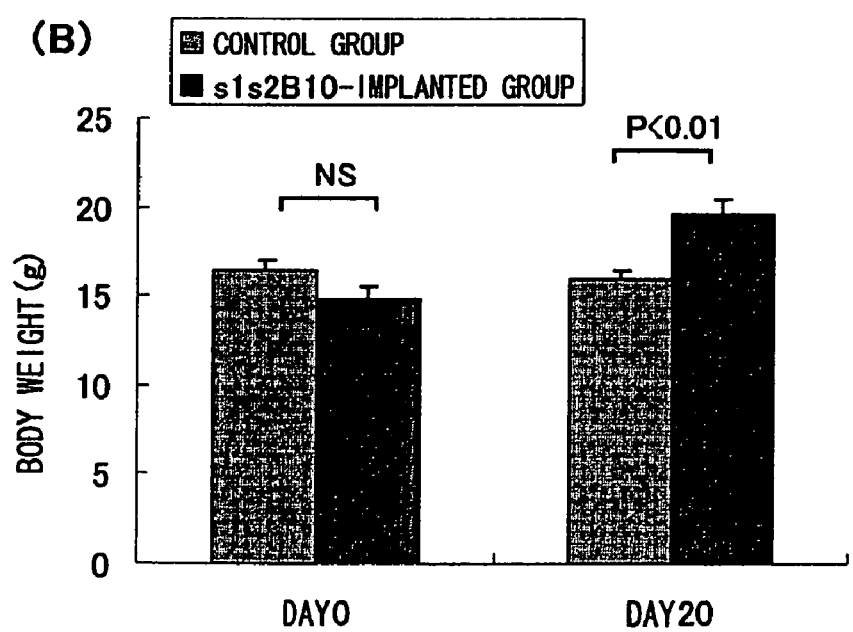

FIG. 16 shows the effect of implanting s1s2B10 insulin-expressing adipocytes in to STZ-induced diabetic mice. Non-gene-transferred cells were implanted as a control. The blood glucose level of the group implanted with insulin-expressing cells tended to decrease from the seventh day of implantation, and a significant hypoglycemic effect was indicated on the 13th and 21st day of implantation (A). The body weight 20 days after implantation was significantly higher in the group implanted with insulin-expressing cells than in the control group, and weight loss due to diabetes was therefore improved (B). The results of examination using AP suggest that this hypoglycemic effect will be maintained for a long period. Therefore, the foreign gene product produced from the implanted primary cultured adipocytes was shown to be able to contribute to the modification of the pathology of the recipient, indicating that this method may be able to treat diabetes.

INDUSTRIAL APPLICABILITY

The present invention established methods of ex vivo transfer of a foreign gene into primary cultured adipocytes suitable for gene therapy, and established primary cultured adipocytes that stably maintain a foreign gene.

The invention claimed is:

1. A population of primary cultured preadipocytes, wherein the preadipocytes are isolated and established from adipose tissue and stably maintain a foreign DNA encoding a protein that is secreted outside of a cell, and wherein the DNA is operably linked to a promoter sequence, wherein the population of primary cultured preadipocytes express the protein encoded by the foreign DNA for about one year in vivo when transplanted in a recipient host.

2. The preadipocyte population of claim 1, wherein the DNA is transferred to the cell by a retroviral vector or adeno-associated viral vector.

3. The preadipocyte population of claim 1, which is used to release the protein into the blood flow of said host.

4. The preadipocyte population of claim 1, wherein the protein is insulin or glucagon-like peptide 1 (GLP-1).

5. A method of producing a population of primary cultured preadipocytes, wherein the method comprises the steps of:
   (1) isolating cells from adipose tissue and establishing a primary culture of preadipocytes; and
   (2) transferring into the preadipocytes a foreign DNA operably linked to a promoter sequence and encoding a protein that is secreted outside of the cell and then stably maintaining the foreign DNA in the genome of the preadipocytes, wherein the population of primary cultured preadipocytes express the protein encoded by the foreign DNA for about one year in vivo when transplanted in a recipient host.

6. The method of claim 5, wherein the foreign gene is transferred by a retroviral vector or adeno-associated viral vector.

7. A population of primary cultured preadipocytes, which is produced by the method of claim 5.

8. An implant composition for gene therapy, wherein the composition comprises a population of primary cultured preadipocytes, which are isolated and established from adipose tissue and stably maintain in the genome a foreign DNA encoding a protein that is secreted outside of the cell, and a pharmaceutically acceptable carrier, wherein the DNA is operably linked to a promoter sequence, wherein the population of primary cultured preadipocytes express the protein encoded by the foreign DNA for about one year in vivo when transplanted in a recipient host.

9. The implant composition of claim 8, which further comprises an extracellular matrix component.

10. The implant composition of claim 8, which further comprises an angiogenesis factor.

11. A population of primary cultured preadipocytes, which is produced by the method of claim 6.

12. A population of primary cultured preadipocytes, wherein the preadipocytes are isolated and established from adipose tissue and stably maintain a foreign DNA encoding a protein that is secreted outside of a cell, wherein the DNA is operably linked to a promoter sequence, wherein the population of primary cultured preadipocytes express the protein encoded by the foreign DNA for about one year in vivo when transplanted in a recipient host, and wherein the population is obtained by ceiling culture.

13. The method of claim 5, wherein the primary culture is established in step (1) by ceiling culture.

* * * * *

SEQUENCE LISTING

<160> NUMBER OF SEQ ID NOS: 11

<210> SEQ ID NO 1
<211> LENGTH: 30
<212> TYPE: DNA
<213> ORGANISM: Artificial
<220> FEATURE:
<223> OTHER INFORMATION: an artificially synthesized oligonucleotide for
      amplifying human insulin gene

<400> SEQUENCE: 1
cataagctta ccatggccct gtggatgcgc                                      30

<210> SEQ ID NO 2
<211> LENGTH: 30
<212> TYPE: DNA
<213> ORGANISM: Artificial
<220> FEATURE:
<223> OTHER INFORMATION: an artificially synthesized oligonucleotide for
      amplifying human insulin gene

<400> SEQUENCE: 2
cattctagac tagttgcagt agttctccag                                      30

<210> SEQ ID NO 3
<211> LENGTH: 37
<212> TYPE: DNA
<213> ORGANISM: Artificial
<220> FEATURE:
<223> OTHER INFORMATION: an artificially synthesized oligonucleotide for
      mutagenesis

<400> SEQUENCE: 3
cttctacaca cccaggacca agcgggaggc agaggac                              37

<210> SEQ ID NO 4
<211> LENGTH: 28
<212> TYPE: DNA
<213> ORGANISM: Artificial
<220> FEATURE:
<223> OTHER INFORMATION: an artificially synthesized oligonucleotide for
      mutagenesis

<400> SEQUENCE: 4
ccctggaggg atcccggcag aagcgtgg                                        28

<210> SEQ ID NO 5
<211> LENGTH: 29
<212> TYPE: DNA
<213> ORGANISM: Artificial
<220> FEATURE:
<223> OTHER INFORMATION: an artificially synthesized oligonucleotide for
      mutagenesis

<400> SEQUENCE: 5
cacctgtgcg gatccgacct ggtggaagc                                       29

<210> SEQ ID NO 6
<211> LENGTH: 83
<212> TYPE: DNA
<213> ORGANISM: Artificial
<220> FEATURE:
<223> OTHER INFORMATION: an artificially synthesized oligonucleotide for
      constructing a gene encoding a secretory human GLP-1

<400> SEQUENCE: 6

```
ttccaccatg ctgctgctgc tgctgctgct gggcctgagg ctacagctct ccctgggcca    60
tgctgaaggg acctttacca gtg                                            83
```

<210> SEQ ID NO 7
<211> LENGTH: 95
<212> TYPE: DNA
<213> ORGANISM: Artificial
<220> FEATURE:
<223> OTHER INFORMATION: an artificially synthesized oligonucleotide for
      constructing a gene encoding a secretory human GLP-1

<400> SEQUENCE: 7

```
aattatcctc ggcctttcac cagccaagca atgaactcct tggcagcttg gccttccaaa    60
taagaactta catcactggt aaaggtccct tcagc                               95
```

<210> SEQ ID NO 8
<211> LENGTH: 20
<212> TYPE: DNA
<213> ORGANISM: Artificial
<220> FEATURE:
<223> OTHER INFORMATION: an artificially synthesized oligonucleotide for
      PCR

<400> SEQUENCE: 8

```
ttccaccatg ctgctgctgc                                                20
```

<210> SEQ ID NO 9
<211> LENGTH: 23
<212> TYPE: DNA
<213> ORGANISM: Artificial
<220> FEATURE:
<223> OTHER INFORMATION: an artificially synthesized oligonucleotide for
      PCR

<400> SEQUENCE: 9

```
aattatcctc ggcctttcac cag                                            23
```

<210> SEQ ID NO 10
<211> LENGTH: 144
<212> TYPE: DNA
<213> ORGANISM: Artificial
<220> FEATURE:
<223> OTHER INFORMATION: a gene encoding a secretory human GLP-1
<220> FEATURE:
<221> NAME/KEY: CDS
<222> LOCATION: (1)..(144)
<223> OTHER INFORMATION:

<400> SEQUENCE: 10

```
atg ctg ctg ctg ctg ctg ctg ggc ctg agg cta cag ctc tcc ctg         48
Met Leu Leu Leu Leu Leu Leu Gly Leu Arg Leu Gln Leu Ser Leu
1               5                   10                  15 ggc cat gct gaa ggg acc ttt acc agt gat gta agt tct tat ttg gaa     96
Gly His Ala Glu Gly Thr Phe Thr Ser Asp Val Ser Ser Tyr Leu Glu
            20                  25                  30 ggc caa gct gcc aag gag ttc att gct tgg ctg gtg aaa ggc cga gga    144
Gly Gln Ala Ala Lys Glu Phe Ile Ala Trp Leu Val Lys Gly Arg Gly
        35                  40                  45
```

<210> SEQ ID NO 11
<211> LENGTH: 48
<212> TYPE: PRT
<213> ORGANISM: Artificial
<220> FEATURE:
<223> OTHER INFORMATION: a secretory human GLP-1

```
<400> SEQUENCE: 11

Met Leu Leu Leu Leu Leu Leu Gly Leu Arg Leu Gln Leu Ser Leu
1               5                   10                  15

Gly His Ala Glu Gly Thr Phe Thr Ser Asp Val Ser Ser Tyr Leu Glu
                20                  25                  30

Gly Gln Ala Ala Lys Glu Phe Ile Ala Trp Leu Val Lys Gly Arg Gly
            35                  40                  45
```